(12) United States Patent
Matsushita et al.

(10) Patent No.: US 8,274,061 B2
(45) Date of Patent: Sep. 25, 2012

(54) SCANNER AND METHOD FOR SETTING VOLTAGE VALUE OF PHOTOMULTIPLIER

(75) Inventors: Masahiro Matsushita, Kanagawa (JP); Yoshifumi Shioe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 3386 days.

(21) Appl. No.: 10/013,505

(22) Filed: Dec. 13, 2001

(65) Prior Publication Data

US 2002/0099511 A1 Jul. 25, 2002

(30) Foreign Application Priority Data

Dec. 25, 2000 (JP) .................................. 2000-393162

(51) Int. Cl.
*G06F 19/26* (2006.01)
(52) U.S. Cl. ....................... 250/458.1; 250/587; 382/128
(58) Field of Classification Search .................. 250/587, 250/458.1; 382/128
See application file for complete search history.

(56) References Cited

U.S. PATENT DOCUMENTS

| | | | | |
|---|---|---|---|---|
| 4,527,060 A | * | 7/1985 | Suzuki et al. ................. | 250/585 |
| 4,922,103 A | * | 5/1990 | Kawajiri et al. .............. | 250/586 |
| 5,198,669 A | * | 3/1993 | Namiki et al. ................ | 250/587 |
| 2002/0168094 A1 | * | 11/2002 | Kaushikkar et al. .......... | 382/128 |

FOREIGN PATENT DOCUMENTS

| | | |
|---|---|---|
| JP | 1-60782 | 12/1989 |
| JP | 1-60784 | 12/1989 |
| JP | 4-3952 | 1/1992 |

* cited by examiner

*Primary Examiner* — David Porta
*Assistant Examiner* — Shun Lee
(74) *Attorney, Agent, or Firm* — Sughrue Mion, PLLC

(57) ABSTRACT

A scanner includes a plurality of laser stimulating ray sources, a sample stage on which a sample containing a labeling substance is to be placed, a scanning mechanism, a photomultiplier for photoelectrically detecting light released from the labeling substance and producing analog image data, an A/D converter for converting the analog image data to digital image data, and a pixel density signal intensity simulating section for effecting simulation based on pre-scan digital image data produced by setting a voltage value of the photomultiplier to a given photomultiplier voltage value G0 to simulate density signal intensity of each pixel of digital image data that would be produced by setting the photomultiplier to a voltage value G different from the voltage value G0. According to the thus constituted scanner, it is possible to determine the voltage value of the photomultiplier simply and rapidly without causing on the degradation of a sample.

4 Claims, 8 Drawing Sheets

SCANNER AND METHOD FOR SETTING VOLTAGE VALUE OF PHOTOMULTIPLIER

BACKGROUND OF THE INVENTION

The present invention relates to a scanner and a method for setting a voltage value of a photomultiplier and, particularly, to such a scanner and a method for setting a voltage value of a photomultiplier which can determine the voltage value of the photomultiplier simply and rapidly without causing degradation of a sample.

DESCRIPTION OF THE PRIOR ART

An autoradiography detecting system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactive labeling substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

Unlike the system using a photographic film, according to the autoradiography detecting system using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence detecting system using a fluorescent substance as a labeling substance instead of a radioactive labeling substance in the autoradiography detecting system is known. According to this system, it is possible to study a genetic sequence, to study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Further, a micro-array detecting system has been recently developed, which comprises the steps of using a spotting device to drop at different positions on the surface of a carrier such as a slide glass plate, a membrane filter or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emitted from a labeling substance such as a fluorescent substance, dye or the like, and analyzing the substance derived from a living organism. This micro-array image detecting system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

The autoradiograpy detecting system, the fluorescence detecting system and the micro-array detecting system are constituted so as to irradiate a sample with a laser beam to stimulate a stimulable phosphor or a labeling substance such as a fluorescent dye and photoelectrically detect stimulated emission released from the stimulable phosphor, fluorescence emission released from the fluorescent dye or the like, thereby producing biochemical analysis data such as image data of a labeling substance and emitted light amount data and for this purpose, a scanner is generally used in these systems so as to scan a sample with a laser beam, photoelectrically detect stimulated emission or fluorescence emission released from the sample using a photomultiplier and produce biochemical analysis data such as image data of a labeling substance and emitted light amount data.

In the thus constituted scanner, the voltage value of a photomultiplier is determined by trial and error by repeating, until a desired image is obtained, the steps of setting a voltage value of the photomultiplier to a reasonable value, irradiating a sample with a laser beam, photoelectrically detecting light released from the sample, reproducing an image based on the thus produced data, viewing the reproduced image, and changing the voltage value of the photomultiplier.

However, such a operation is not only very troublesome and time-consuming but also causes the degradation of the sample because a stimulable phosphor releases radiation energy stored therein upon being irradiated with a laser beam, thereby decreasing the radiation energy stored therein and the amount of fluorescence emission released from a fluorescent substance when being repeatedly irradiated with a laser beam.

SUMMARY OF THE INVENTION

It is therefore an object of the present invention to provide a scanner and a method for setting a voltage value of a photomultiplier which can determine the voltage value of the photomultiplier simply and rapidly without causing degradation of a sample.

The above and other objects of the present invention can be accomplished by a scanner comprising at least one laser stimulating ray source for emitting a laser beam, a sample stage on which a sample containing a labeling substance is to be placed, a scanning means for moving the sample stage so that the sample placed on the sample stage can be scanned with the laser beam emitted from the at least one laser stimulating ray source, a photomultiplier for photoelectrically detecting light released from the labeling substance contained in the sample upon being scanned with the laser beam and producing analog image data, and an A/D converter for converting the analog image data produced by the photomultiplier to digital image data the scanner further comprising pixel density signal intensity simulating means for effecting simulation based on pre-scan digital image data produced by setting a voltage value of the photomultiplier to a given voltage value G0, scanning the sample placed on the sample stage with the laser beam emitted from the at least one laser stimulating ray source, thereby effecting pre-scanning, and photoelectrically detecting light released from the labeling substance contained in the sample as a result of the pre-scanning by the photomultiplier, which simulation uses the pre-scan digital image data produced when the voltage value of the photomultiplier is set to G0 to simulate density signal intensity of each pixel of digital image data that would be produced by setting the photomultiplier to a voltage value G different from the voltage value G0, scanning the sample placed on the sample stage with the laser beam emitted from the at least one laser stimulating ray source, photoelectrically detecting light released from the labeling substance contained in the sample by the photomultiplier whose voltage value is set to G to produce analog image data, and digitizing the analog image data by the A/D converter.

According to this aspect of the present invention, the scanner includes pixel density signal intensity simulating means for effecting simulation based pre-scan digital image data produced by setting a voltage value of the photomultiplier to a given voltage value G0, scanning the sample placed on the sample stage with the laser beam emitted from the at least one laser stimulating ray source, thereby effecting pre-scanning, and photoelectrically detecting light released from the labeling substance contained in the sample as a result of the pre-scanning by the photomultiplier, which simulation uses the pre-scan digital image data produced when the voltage value of the photomultiplier is set to G0 to simulate density signal intensity of each pixel of digital image data that would be produced by setting the photomultiplier to a voltage value G different from the voltage value G0, scanning the sample placed on the sample stage with the laser beam emitted from the at least one laser stimulating ray source, photoelectrically detecting light released from the labeling substance contained in the sample by the photomultiplier whose voltage value is set to G to produce analog image data, and digitizing the analog image data by the A/D converter. Therefore, since a photomultiplier voltage value G capable of producing an image having desired contrast can be determined by using digital image data produced by specifying a moderate but arbitrary photomultiplier voltage value G0 and effecting pre-scanning to simulate the density signal intensity of each pixel of digital image data that would be produced by using the photomultiplier with its voltage value set to a voltage value G different from the voltage value G0 used for the pre-scanning by the pixel density signal intensity simulating means, the voltage value of the photomultiplier can be set to a proper value without repeating the pre-scanning.

In a preferred aspect of the present invention, the pixel density signal intensity simulating means comprises density signal intensity shift value calculating means for calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier to a photomultiplier voltage value G different from the given photomultiplier voltage value G0 to produce analog image data, and digitizing the analog image data by the A/D converter from the density signal intensity of each pixel of the digital image data produced by the pre-scanning, and pixel density signal intensity correcting means for correcting the density signal intensity of each pixel of the digital image data produced by the pre-scanning based on the density signal intensity shift value calculated by the density signal intensity shift value calculating means and simulating density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter.

According to this preferred aspect of the present invention, the pixel density signal intensity simulating means comprises density signal intensity shift value calculating means for calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter from the density signal intensity of each pixel of the digital image data produced by the pre-scanning, and pixel density signal intensity correcting means for correcting the density signal intensity of each pixel of the digital image data produced by the pre-scanning based on the density signal intensity shift value calculated by the density signal intensity shift value calculating means and simulating density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter. As a result, a photomultiplier voltage value G capable of producing an image having desired contrast can be determined by calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter from the density signal intensity of each pixel of the digital image data produced by the pre-scanning by the density signal intensity shift value calculating means, correcting the density signal intensity of each pixel of the digital image data produced by the pre-scanning by the pixel density signal intensity correcting means, thereby producing digital image data that would be produced using photomultiplier set to a photomultiplier voltage value G different from the given photomultiplier voltage value G0 and, therefore, the voltage value of the photomultiplier can be set to a proper value without repeating the pre-scanning.

In a further preferred aspect of the present invention, the scanner further comprises a display means and an image is produced based on digital image data produced by correcting density signal intensity of each pixel of digital image data produced by scanning the sample placed on the sample stage with the laser beam emitted from the at least one laser stimulating ray source and photoelectrically detecting light released from the labeling substance contained in the sample by the photomultiplier set to the given photomultiplier voltage value G0 by the pixel density signal intensity correcting means and displayed on the display means.

According to this preferred aspect of the present invention, since the scanner further comprises a display means and an image is produced based on digital image data produced by correcting density signal intensity of each pixel of digital image data produced by scanning the sample placed on the sample stage with the laser beam emitted from the at least one laser stimulating ray source and photoelectrically detecting light released from the labeling substance contained in the sample by the photomultiplier whose voltage value is set to the given photomultiplier voltage value G0 by the pixel density signal intensity correcting means and displayed on the display means, the user can view an image displayed on the display means such as a CRT and very easily determine a desired photomultiplier voltage value G capable of producing an image having proper contrast.

In a further preferred aspect of the present invention, the scanner further comprises photomultiplier voltage value setting means for setting the photomultiplier voltage value G of the photomultiplier based on the density signal intensity of each pixel of the digital image data simulated by the pixel density signal intensity simulating means.

In a further preferred aspect of the present invention, the scanner comprises two or more laser stimulating ray sources for emitting laser beams having different wavelengths from each other and the pre-scanning is effected for each wavelength of the laser beams emitted from the two or more laser stimulating ray sources for scanning the sample placed on the sample stage and the pixel density signal intensity simulating means is constituted so as to effect simulation based on pre-scan digital image data produced by photoelectrically detecting light released from the labeling substance contained in the sample as a result of the pre-scanning with a laser beam emitted from each of the two or more laser stimulating ray sources by the photomultiplier whose voltage value is set to the given photomultiplier voltage value G0, which simulation uses the pre-scan digital image data to simulate density signal intensity of each pixel of digital image data that would be produced by scanning the sample placed on the sample stage with the laser beam emitted from each of the two or more laser stimulating ray sources, photoelectrically detecting light released from the labeling substance contained in the sample by the photomultiplier set to a photomultiplier voltage value G different from the given photomultiplier voltage value G0 to produce analog image data, and digitizing the analog image data by the A/D converter.

In the case where the sample placed on the sample stage is scanned with laser beams having different wavelengths from each other, even if the voltage value of the photomultiplier is the same, if the sample is scanned with laser beams having different wavelengths, the density signal intensity of each pixel of produced digital image data is different and, therefore, the density signal intensity of each pixel of digital image data produced by the pre-scanning using the photomultiplier set to the given photomultiplier voltage value G0 changes. However, according to this preferred aspect of the present invention, the scanner comprises two or more laser stimulating ray sources and the pre-scanning is effected for each wavelength of the laser beams emitted from the two or more laser stimulating ray sources for scanning the sample placed on the sample stage and the pixel density signal intensity simulating means is constituted so as to effect simulation based on digital image data produced by photoelectrically detecting light released from the labeling substance contained in the sample as a result of the pre-scanning with a laser beam emitted from each of the two or more laser stimulating ray sources by the photomultiplier set to the given photomultiplier voltage value G0, which simulation uses the produced digital image data to simulate density signal intensity of each pixel of digital image data that would be produced by scanning the sample placed on the sample stage with the laser beam emitted from each of the two or more laser stimulating ray sources, photoelectrically detecting light released from the labeling substance contained in the sample by the photomultiplier set to a photomultiplier voltage value G different from the given photomultiplier voltage value G0 to produce analog image data, and digitizing the analog image data by the A/D converter. Therefore, in the case where a sample placed on the sample stage is scanned with laser beams having different wavelengths from each other, it is possible to produce an image having desired contrast.

In a further preferred aspect of the present invention, the scanner further comprises photomultiplier voltage value setting means for setting a photomultiplier voltage value of the photomultiplier based on density signal intensity of each pixel of digital image data simulated by the pixel density signal intensity simulating means for each wavelength of laser beams emitted from the two or more laser stimulating ray sources.

In a further preferred aspect of the present invention, the density signal intensity shift value calculating means is constituted so as to calculate a density signal intensity shift value $\Delta QL$ of each pixel in accordance with the following formula wherein G0 is the given photomultiplier voltage value, G is a photomultiplier voltage value different from the given photomultiplier voltage value G0, B is the number of bits and L is latitude $$\Delta QL = 2^B/L * \{\log_{10}(G/G0)\}$$

In a further preferred aspect of the present invention, the pixel density signal intensity correcting means is constituted so as to simulate, in accordance with the following formula, density signal intensity $QLi_\lambda$ (where $\lambda$ is a wavelength of the laser beam emitted from the at least one laser stimulating ray source.) of each pixel of digital image data that would be produced by photoelectrically detecting light released from the sample by the photomultiplier whose voltage value is set to a photomultiplier voltage value G different from the given photomultiplier voltage value G0 to produce analog image data and digitizing the analog image data by the A/D converter, wherein $QLi0_\lambda$ is density signal intensity of each pixel of the digital image data produced by the pre-scanning $$QLi_\lambda = QLi0_\lambda + \Delta QL.$$

In a further preferred aspect of the present invention, the sample containing the labeling substance is constituted as a sample containing a fluorescent dye.

In a further preferred aspect of the present invention, the sample containing the labeling substance is constituted as a micro-array including a substrate on which a plurality of spots of a specimen selectively labeled with a fluorescent dye are formed.

In a further preferred aspect of the present invention, the sample containing the labeling substance is constituted as a stimulable phosphor sheet formed with a stimulable phosphor layer in which radiation energy is stored.

The above and other objects of the present invention can be also accomplished by a method for setting a voltage value of a photomultiplier comprising the steps of setting a voltage value of a photomultiplier to a given photomultiplier voltage value G0, scanning a sample containing a labeling substance and placed on a sample stage with a laser beam, thereby effecting pre-scanning, photoelectrically detecting light released from the labeling substance contained in the sample as a result of the pre-scanning by the photomultiplier whose voltage value is set to the given photomultiplier voltage value G0 to produce analog image data, digitizing the analog image data by an A/D converter to produce digital image data, simulating, based on density signal intensity of each pixel of the digital image data produced by the pre-scanning, density signal intensity of each pixel of digital image data that would be produced by scanning the sample placed on the sample stage with a laser beam, photoelectrically detecting light released from the labeling substance contained in the sample by the photomultiplier set to a photomultiplier voltage value G different from the given photomultiplier voltage value G0 to produce analog image data and digitizing the analog image data by the A/D converter, determining a photomultiplier voltage value G of the photomultiplier in accordance with the simulated density signal intensity of each pixel of the digital image data, and setting the voltage value of the photomultiplier.

According to this aspect of the present invention, the method for setting a voltage value of a photomultiplier comprising the steps of setting a voltage value of a photomultiplier to a given photomultiplier voltage value G0, scanning a sample containing a labeling substance and placed on a sample stage with a laser beam, thereby effecting pre-scanning, photoelectrically detecting light released from the labeling substance contained in the sample as a result of the pre-scanning by the photomultiplier whose voltage value is set to the given photomultiplier voltage value G0 to produce analog image data, digitizing the analog image data by an A/D converter to produce digital image data, simulating, based on density signal intensity of each pixel of the digital image data produced by the pre-scanning, density signal intensity of each pixel of digital image data that would be produced by scanning the sample placed on the sample stage with a laser beam, photoelectrically detecting light released from the labeling substance contained in the sample by the photomultiplier whose voltage value is set to a photomultiplier voltage value G different from the given photomultiplier voltage value G0 to produce analog image data and digitizing the analog image data by the A/D converter, determining a photomultiplier voltage value G of the photomultiplier in accordance with the simulated density signal intensity of each pixel of the digital image data, and setting the voltage value of the photomultiplier. Therefore, a photomultiplier voltage value G capable of producing an image having desired contrast can be set by simulating, based on digital image data produced by specifying a moderate but arbitrary photomultiplier voltage value G0 and effecting the pre-scanning, density signal intensity of each pixel of digital image data that would be produced using the photomultiplier whose voltage value is set to a photomultiplier voltage value G different from the photomultiplier voltage value G0 used for the pre-scanning by the pixel density signal intensity simulating means and, therefore, the voltage value of the photomultiplier can be set to a proper value without repeating the pre-scanning.

In a preferred aspect of the present invention, the method for setting a voltage value of a photomultiplier further comprises the steps of calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter from the density signal intensity of each pixel of the digital image data produced by the pre-scanning, correcting the density signal intensity of each pixel of digital image data produced by the pre-scanning in accordance with the density signal intensity shift value, and simulating density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter.

According to this preferred aspect of the present invention, the method for setting a voltage value of a photomultiplier further comprises the steps of calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier whose voltage value is set to a photomultiplier voltage value G different from the given photomultiplier voltage value G0 to produce analog image data, and digitizing the analog image data by the A/D converter from the density signal intensity of each pixel of the digital image data produced by the pre-scanning, correcting the density signal intensity of each pixel of digital image data produced by the pre-scanning in accordance with the density signal intensity shift value, and simulating density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter. Therefore, a photomultiplier voltage value G capable of producing an image having desired contrast can be determined by calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter from the density signal intensity of each pixel of the digital image data produced by the pre-scanning, correcting the density signal intensity of each pixel of the digital image data produced by the pre-scanning, thereby producing digital image data that would be produced using photomultiplier whose voltage value is set to a photomultiplier voltage value G different from the given photomultiplier voltage value G0 and, therefore, the voltage value of the photomultiplier can be set to a proper value without repeating the pre-scanning.

In a further preferred aspect of the present invention, the method for setting a voltage value of a photomultiplier further comprises the step of displaying an image based on digital image data whose density signal intensity of each pixel has been simulated and the photomultiplier voltage value G is determined based on the thus displayed image and the voltage value of the photomultiplier is set.

According to this preferred aspect of the present invention, since the method for setting a voltage value of a photomultiplier further comprises the step of displaying an image based on digital image data whose density signal intensity of each pixel has been simulated and the photomultiplier voltage value G is determined based on the thus displayed image and the voltage value of the photomultiplier is set, the user can view an image displayed on the display means such as a CRT and very easily determine a desired photomultiplier voltage value G capable of producing an image having proper contrast.

In a further preferred aspect of the present invention, the method for setting a voltage value of a photomultiplier comprises the steps of effecting pre-scanning for each wavelength of laser beams for scanning the sample placed on the sample stage, producing digital image data by photoelectrically detecting light released from the labeling substance contained in the sample by the photomultiplier set to the given photomultiplier voltage value G0 to produce analog image data and digitizing the analog image data by the A/D converter, simulating, based on the digital image data produced by the pre-scanning, density signal intensity of each pixel of digital image data that would be produced by scanning the sample placed on the sample stage with the laser beam emitted from each of the two or more laser stimulating ray sources, photoelectrically detecting light released from the labeling substance contained in the sample by the photomultiplier set to a photomultiplier voltage value G different from the given photomultiplier voltage value G0 to produce analog image data, and digitizing the analog image data by the A/D converter, determining a photomultiplier voltage value of the photomultiplier in accordance with the thus simulated density signal intensity of each pixel of the digital image data, and setting a voltage value of the photomultiplier.

When the sample is scanned with laser beams having different wavelengths, even if the voltage value of the photomultiplier is the same, the density signal intensity of each pixel of produced digital image data is different and, therefore, the density signal intensity of each pixel of digital image data produced by the pre-scanning using the photomultiplier set to the given photomultiplier voltage value G0 changes. However, according to this preferred aspect of the present invention, the method for setting a voltage value of a photomultiplier comprises the step of effecting pre-scanning for each wavelength of laser beams for scanning the sample placed on the sample stage, producing digital image data by photoelectrically detecting light released from the labeling substance contained in the sample by the photomultiplier set to the given photomultiplier voltage value G0 to produce analog image data and digitizing the analog image data by the A/D converter, simulating, based on the digital image data produced by the pre-scanning, density signal intensity of each pixel of digital image data that would be produced by scanning the sample placed on the sample stage with the laser beam emitted from each of the two or more laser stimulating ray sources, photoelectrically detecting light released from the labeling substance contained in the sample by the photomultiplier set to a photomultiplier voltage value G different from the given photomultiplier voltage value G0 to produce analog image data, and digitizing the analog image data by the A/D converter, determining a photomultiplier voltage value of the photomultiplier in accordance with the thus simulated density signal intensity of each pixel of the digital image data, and setting a voltage value of the photomultiplier. Therefore, in the case where a sample placed on the sample stage is scanned with laser beams having different wavelengths from each other, it is possible to produce an image having desired contrast.

In a further preferred aspect of the present invention, the method for setting a voltage value of a photomultiplier further comprises the step of displaying an image based on digital image data whose density signal intensity of each pixel has been simulated for each wavelength of the laser beams, and a photomultiplier voltage value of the photomultiplier is determined in accordance with the thus displayed image and a voltage value of the photomultiplier is set.

In a further preferred aspect of the present invention, a density signal intensity shift value $\Delta QL$ of each pixel is calculated in accordance with the following formula wherein G0 is the given photomultiplier voltage value, G is a photomultiplier voltage value different from the given photomultiplier voltage value G0, B is the number of bits and L is latitude $$\Delta QL = 2^B/L \ast \{\log_{10}(G/G0)\}$$

In a further preferred aspect of the present invention, density signal intensity $QLi_\lambda$ (where $\lambda$ is a wavelength of the laser beam emitted from the at least one laser stimulating ray source.) of each pixel of digital image data that would be produced by photoelectrically detecting light released from the sample by the photomultiplier set to a photomultiplier voltage value G different from the given photomultiplier voltage value G0 to produce analog image data and digitizing the analog image data by the A/D converter is simulated in accordance with the following formula wherein $QLi0_\lambda$ is density signal intensity of each pixel of the digital image data produced by the pre-scanning $$QLi_\lambda = QLi0_\lambda + \Delta QL.$$

In a further preferred aspect of the present invention, the sample containing the labeling substance is constituted as a sample containing a fluorescent dye.

In a further preferred aspect of the present invention, the sample containing the labeling substance is constituted as a micro-array including a substrate on which a plurality of spots of a specimen selectively labeled with a fluorescent dye are formed.

In a further preferred aspect of the present invention, the sample containing the labeling substance is constituted as a stimulable phosphor sheet formed with a stimulable phosphor layer in which radiation energy is stored.

The above and other objects and features of the present invention will become apparent from the following description made with reference to the accompanying drawings.

DESCRIPTION OF THE PREFERRED EMBODIMENT

Figure 1:
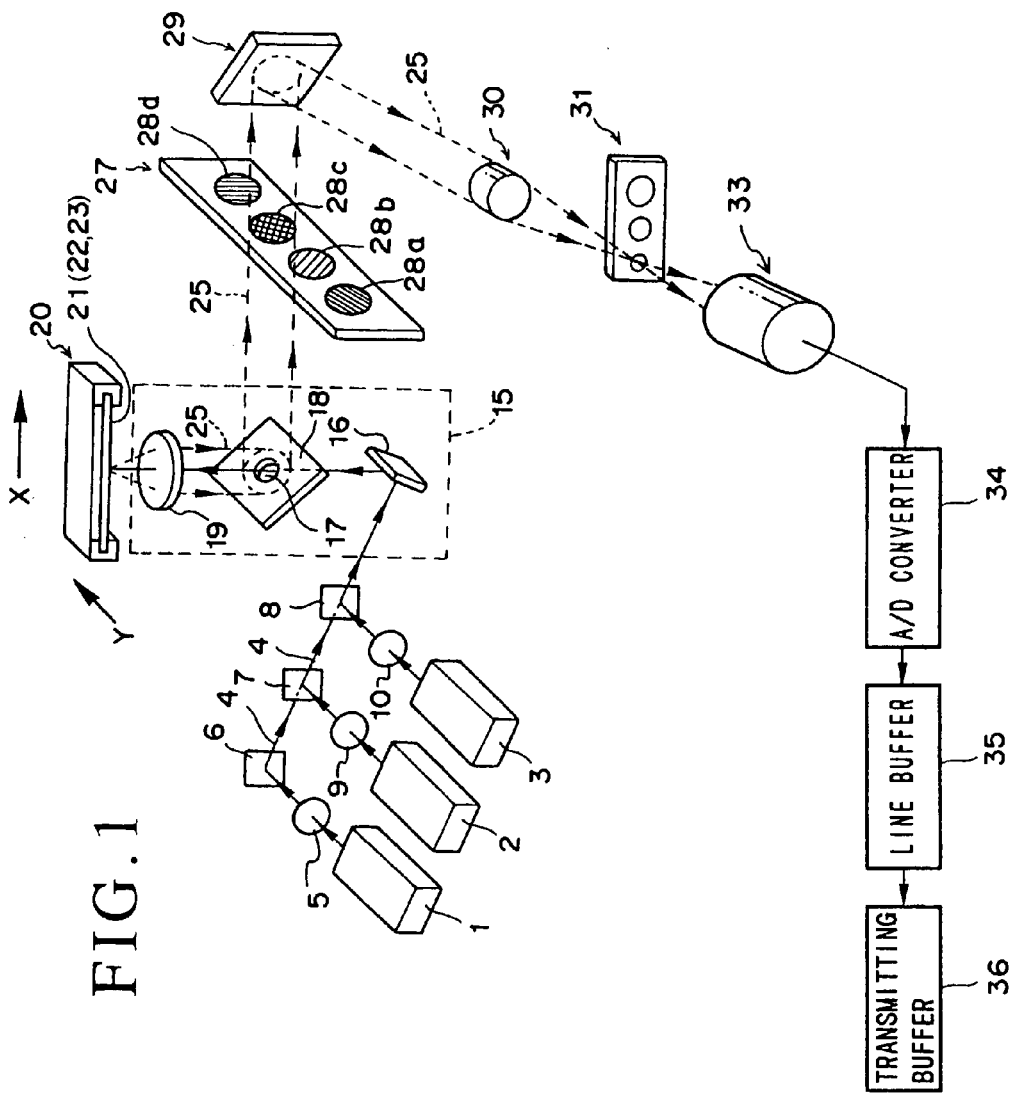
FIG. 1 is a schematic perspective view showing a scanner which is a preferred embodiment of the present invention.

FIG. 1 is a schematic perspective view showing a scanner which is a preferred embodiment of the present invention.

As shown in FIG. 1, a scanner according to this embodiment includes a first laser stimulating ray source 1 for emitting a laser beam having a wavelength of 640 nm, a second laser stimulating ray source 2 for emitting a laser beam having a wavelength of 532 nm and a third laser stimulating ray source 3 for emitting a laser beam having a wavelength of 473 nm. In this embodiment, the first laser stimulating ray source 1 constituted by a semiconductor laser beam source and the second laser stimulating ray source 2 and the third laser stimulating ray source 3 are constituted by a second harmonic generation element.

A laser beam 4 emitted from the first laser stimulating source 1 passes through a collimator lens 5, thereby being made a parallel beam, and is reflected by a mirror 6. A first dichroic mirror 7 for transmitting light having a wavelength of 640 nm but reflecting light having a wavelength of 532 nm and a second dichroic mirror 8 for transmitting light having a wavelength equal to and longer than 532 nm but reflecting light having a wavelength of 473 nm are provided in an optical path of the laser beam 4 reflected by the mirror 6. The laser beam 4 emitted from the first laser stimulating ray source 1 passes through the first dichroic mirror 7 and the second dichroic mirror 8 and enters an optical unit 15.

On the other hand, the laser beam 4 emitted from the second laser stimulating ray source 2 passes through a collimator lens 9, thereby being made a parallel beam, and is reflected by the first dichroic mirror 7, thereby changing its direction by 90 degrees. The laser beam 4 then passes through the second dichroic mirror 8 and enters the optical unit 15.

Further, the laser beam 4 emitted from the third laser stimulating ray source 3 passes through a collimator lens 10, thereby being made a parallel beam, and is reflected by the second dichroic mirror 8, thereby changing its direction by 90 degrees.

The optical unit 15 includes a mirror 16, a perforated mirror 18 whose center portion is formed with a hole 17 and a lens 19. The laser beam 4 entering the optical unit 15 is reflected by the mirror 16 and passes through the hole 17 formed in the perforated mirror 18 and the lens 19, thereby entering a sample carrier 21 set on a sample stage 20. The sample stage 20 is constituted so as to be movable by a scanning mechanism (not shown) in the X direction and the Y direction in FIG. 1.

The scanner according to this embodiment is constituted so as to produce image data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye and to also produce image data for biochemical analysis by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye. The scanner according to this embodiment is further constituted so as to produce image data for biochemical analysis by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor.

A micro-array is prepared in the following manner, for example.

First, a specimen solution containing different cDNA probes is spot-like dropped onto the slide glass plate, whereby a plurality of spots are formed on the slide glass plate.

On the other hand, a specimen of RNA is extracted from biological cells, and mRNA having poly A at 3' terminal is extracted from the RNA. Then, cDNA is synthesized from the thus extracted mRNA having poly A at 3' terminal in the presence of a labeling substance, Cy3 (registered trademark), to prepare first target DNA labeled with Cy3.

Further, a specimen of RNA is extracted from biological cells, and mRNA having poly A at 3' terminal is extracted from the RNA. Then, cDNA is synthesized from the thus extracted mRNA having poly A at 3' terminal in the presence of a labeling substance, Cy5 (registered trademark), to prepare second target DNA labeled with Cy5.

The thus prepared first target DNA and second target DNA are mixed and the thus mixed solution is gently loaded onto the surface of the slide glass plate 23 on which cDNAs, specific binding substances, are spotted, and then hybridization is performed.

On the other hand, an electrophoresis image of denatured DNA fragments labeled with a fluorescent dye is recorded in a transfer support in the following manner, for example.

First, a plurality of DNA fragments containing a specific gene are separated and distributed on a gel support medium by means of electrophoresis and are denatured by alkali processing to form single-stranded DNA.

Then, according to the known Southern blotting method, the gel support and a transfer support are stacked to transfer at least a part of the denatured DNA fragments onto the transfer support and the transferred DNA fragments are fixed on the transfer support by heating and irradiating with an ultraviolet ray.

Further, probes prepared by labeling DNA or RNA with fluorescent dye, which is complementary to the DNA containing the specific gene, and the denatured DNA fragments on the transfer support are hybridized by heating to form double-stranded DNA fragments or combined DNA and RNA. Then, DNA or RNA which is complementary to the DNA containing DNA of the specific gene is labeled with a fluorescent dye such as Fluorescein, Rhodamine or Cy-5 to prepare the probes. Since the denatured DNA fragments are fixed on the transfer support at this time, only the DNA fragments which are complimentary to the probe DNA or probe RNA are hybridized to acquire the fluorescently labeled probe. Then, the probes which have not formed hybrids are removed by washing with a proper solution and only the DNA fragments having a specific gene form hybrids with the fluorescently labeled DNA or RNA on the transfer support to be fluorescently labeled. The thus obtained transfer support records an electrophoresis image of the denatured DNA labeled with fluorescent dye.

Further, locational information regarding a radioactive labeling substance is recorded in a stimulable phosphor layer formed on the stimulable sheet in following manner, for example.

The surface of a substrate such as a membrane filter is pretreated and then cDNAs which are specific binding substances, each of which has a known base sequence and is different from the others, are spotted onto predetermined positions on the surface of the substrate such as a membrane filter using a spotter device.

On the other hand, a specimen of RNA is extracted from biological cells, and mRNA having poly A at 3' terminal is extracted from the RNA. Then, cDNA is synthesized from the thus extracted mRNA having poly A at 3' terminal in the presence of a radioactive labeling substance to prepare probe DNA labeled with the radioactive labeling substance.

A solution of the thus obtained probe DNA labeled with the radioactive labeling substance is prepared, and is gently loaded onto the surface of the substrate such as a membrane filter on which cDNAs, specific binding substances, are spotted, and then hybridization is performed.

A stimulable phosphor layer formed on a stimulable phosphor sheet is then superimposed on the surface of the substrate such as a membrane filter containing a hybridized specimen and they are held for a certain period of time, whereby at least a part of radiation released from the radioactive labeling substance on the substrate such as a membrane filter is absorbed in the stimulable phosphor layer formed on the stimulable phosphor sheet and locational information of the radioactive labeling substance is recorded in the stimulable phosphor layer.

When the laser beam 4 is impinged on the sample 22 from the optical unit 15, a fluorescent substance is excited by the laser beam 4 to release fluorescence emission in the case where the sample 22 is a micro-array or a fluorescence sample. On the other hand, in the case where the sample 22 is a stimulable phosphor sheet, stimulable phosphors contained in the stimulable phosphor sheet are excited by the laser beam 4 to release stimulated emission.

The fluorescence emission or the stimulated emission 25 released from the sample 22 is made into a parallel beam, by the lens 19 of the optical unit 15 and reflected by the perforated mirror 18, thereby entering one of four filters 28a, 28b, 28c and 28d of a filter unit 27.

The filter unit 27 is constituted to be laterally movable in FIG. 1 by a motor (not shown) so that a predetermined one of the filters 28a, 28b, 28c and 28d is located in the optical path of the fluorescence emission or the stimulated emission 25 depending upon the kind of the laser stimulating ray source to be used.

The filter 28a is used for reading fluorescence emission released from fluorescent substance contained in the sample 22 upon being excited using the first laser stimulating ray source 1 and has a property to cut off light having a wavelength of 640 nm but transmit light having a wavelength longer than 640 nm.

The filter 28b is used for reading fluorescence emission released from fluorescent substance contained in the sample 22 upon being excited using the second laser stimulating ray source 2 and has a property to cut off light having a wavelength of 532 nm but transmit light having a wavelength longer than 532 nm.

The filter 28c is used for reading fluorescence emission released from fluorescent substance contained in the sample 22 upon being excited using the third laser stimulating ray source 3 and has a property to cut off light having a wavelength of 473 nm but transmit light having a wavelength longer than 473 nm.

The filter 28d is used in the case where the sample 22 is a stimulable phosphor sheet for reading stimulated emission released from stimulable phosphor contained in the stimulable phosphor sheet upon being excited using the first laser stimulating ray source 1 and has a property to transmit only light having a wavelength corresponding to that of stimulated emission emitted from stimulable phosphor but cut off light having a wavelength of 640 nm.

Therefore, in accordance with the kind of a stimulating ray source to be used, namely, depending upon whether the image to be read is a fluorescent image or an image regarding locational information of a radioactive labeling substance and the kind of fluorescent substance labeling a specimen, one of these filters 28a, 28b, 28c, 28d is selectively used, thereby cutting light of wavelengths which cause noise.

After fluorescence emission or stimulated emission 25 passes through one of the filters 28a, 28b, 28c, 28d, whereby light of a predetermined wavelength region is cut, the fluorescence emission or the stimulated emission 25 advances to a mirror 29 and is reflected thereby to be focused by a lens 30.

The lens 19 and the lens 30 constitute a confocal optical system. The reason for employing a confocal optical system is to enable fluorescence emission emitted from a minute spot formed on a slide glass plate to be read with a high S/N ratio when the sample 22 is a micro-array including the slide glass plate 23 as a substrate.

A confocal switching member 31 is provided at the focal point of the lens 30.

Figure 2:
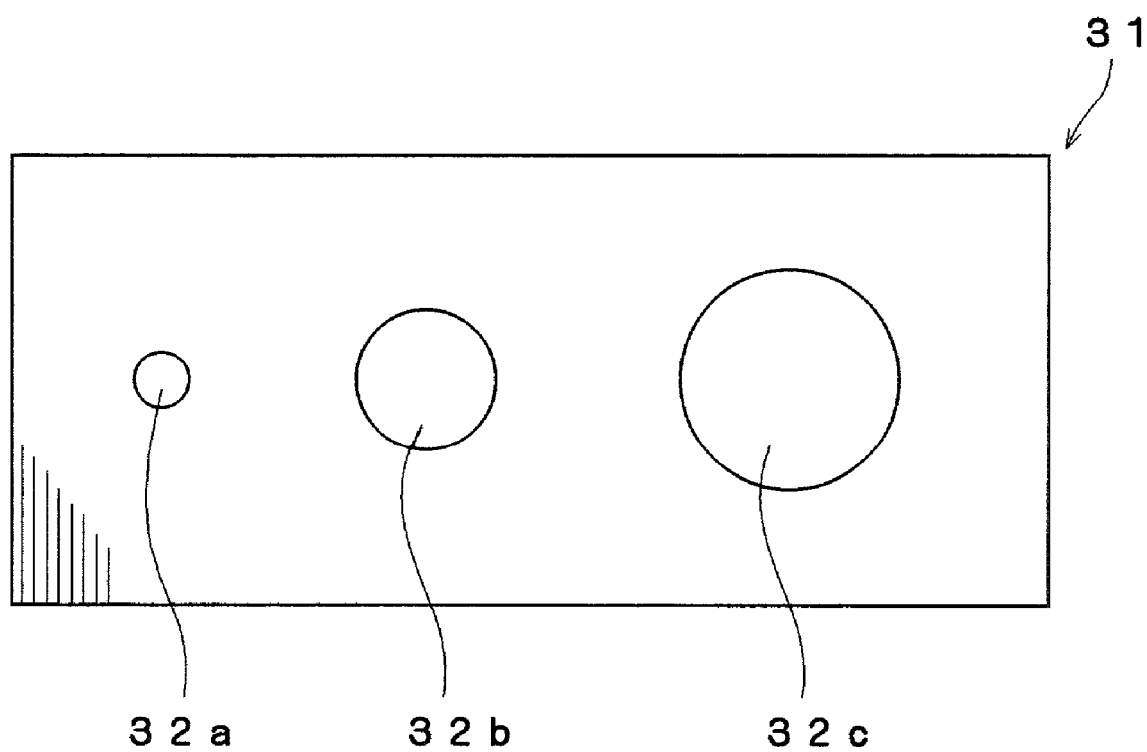
FIG. 2 is a schematic front view showing a confocal switching member.

FIG. 2 is a schematic front view showing the confocal switching member 31.

As shown in FIG. 2, the confocal switching member 31 is formed plate-like and with three pinholes 32a, 32b, 32c.

The pinhole 32a having the smallest diameter is located in a light path of fluorescence emission emitted from the micro-array when the sample is a micro-array including a slide glass plate as a substrate and the pinhole 32c having the largest diameter is located in a light path of fluorescence emission emitted from a transfer support when the sample is a fluorescence sample including a transfer support as a substrate.

Further, the pinhole 32b having an intermediate diameter is located in a light path of a stimulated emission released from a stimulable phosphor layer when the sample is a stimulable phosphor sheet.

In this manner, the confocal switching member 31 is provided at the focal point of the lens 30 and the pinhole 32a having the smallest diameter is located in the light path of fluorescence emission when the sample 22 is a micro-array including a slide glass plate as a substrate. This is because when the sample 22 is a micro-array including a slide glass plate 23 as a substrate, fluorescence emission is emitted from the surface of the slide glass plate when the fluorescent dye is excited with the laser beam 4 and the depth of the light emitting points in the slide glass plate is substantially constant, so that it is preferable to use a confocal optical system to focus an image on the pinhole 32a having the smallest diameter for improving the S/N ratio.

On the other hand, the pinhole 32c is located in the light path of fluorescence emission when the sample 22 is a fluorescence sample including a transfer support as a substrate. This is because when the sample 22 is a fluorescence sample including a transfer support as a substrate, the positions of the light emitting points fluctuate in the depth direction when the fluorescent dye is excited with the laser beam 4 because the fluorescent substance are distributed in the depth direction of the transfer support, so that it is impossible to focus an image on a pinhole having a small diameter even when a confocal optical system is used, and a fluorescent light emitted from the specimen is cut if a pinhole having a small diameter is used, whereby signals having a sufficient intensity cannot be obtained and, therefore, it is necessary to use the pinhole 32c having the largest diameter.

Further, in the case where the sample 22 is a stimulable phosphor sheet, the pinhole 32b having an intermediate diameter is located in a light path of a stimulated emission. This is because when the sample 22 is a stimulable phosphor sheet, the positions of the light emitting points fluctuate in the depth direction when a stimulable phosphor contained in the stimulable phosphor layer is excited with the laser beam 4 because the light emitting points of a stimulated emission are distributed in the depth direction of the stimulable phosphor layer, so that it is impossible to focus an image on a pinhole having a small diameter even when a confocal optical system is used, and the stimulated emission emitted from the specimen is cut if a pinhole having a small diameter is used, whereby signals having a sufficient intensity cannot be obtained by photoelectrically detecting the stimulated emission but the distribution of the light emitting points in the depth direction and the fluctuation in positions of the light emitting points in the depth direction are no so great as those for reading a fluorescent image carried in the transfer support or the gel support and, therefore, it is preferable to employ the pinhole 32b having an intermediate diameter.

The fluorescence emission or stimulated emission 25 passing through the confocal switching member 31 is photoelectrically detected by a photomultiplier 33, thereby producing analog image data.

The analog image data produced by the photomultiplier 33 are converted by an A/D converter 34 into digital image data and the digital image data are forwarded to a line buffer 35 and stored therein.

The line buffer 35 temporarily stores image data corresponding to one scanning line. When the digital image data corresponding to one scanning line have been stored in the line buffer 35 in the above described manner, the line buffer 35 outputs the digital image data to a transmitting buffer 36 whose capacity is greater than that of the line buffer 35 and when the transmitting buffer 36 has stored a predetermined amount of the digital image data, it outputs the digital image data to an image processing apparatus 37.

Figure 3:
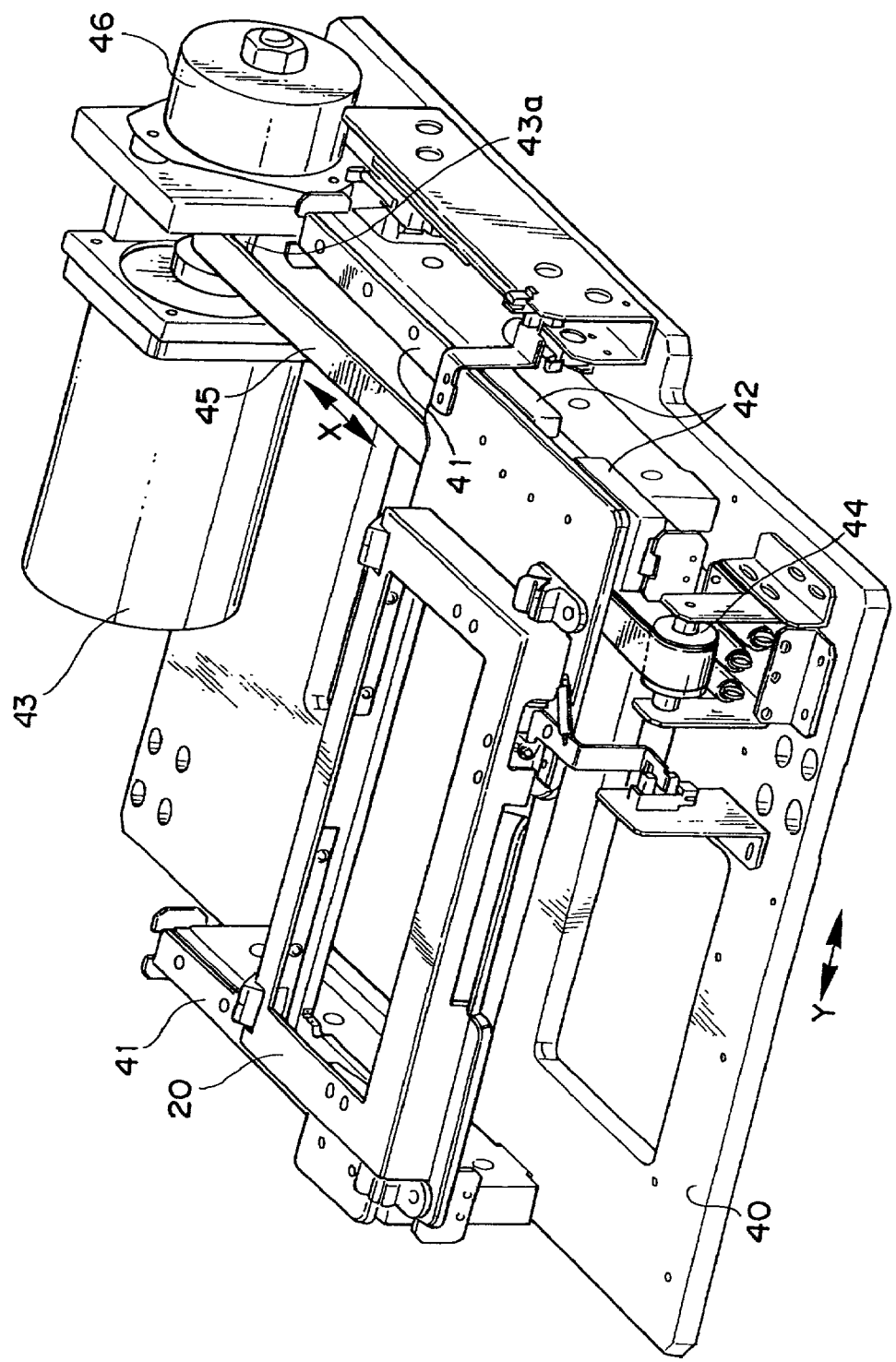
FIG. 3 is a schematic perspective view showing the details of a main scanning mechanism that is part of a scanning mechanism of a sample stage.

FIG. 3 is a schematic perspective view showing the details of a main scanning mechanism that is part of a scanning mechanism of the sample stage 20.

Figure 4:
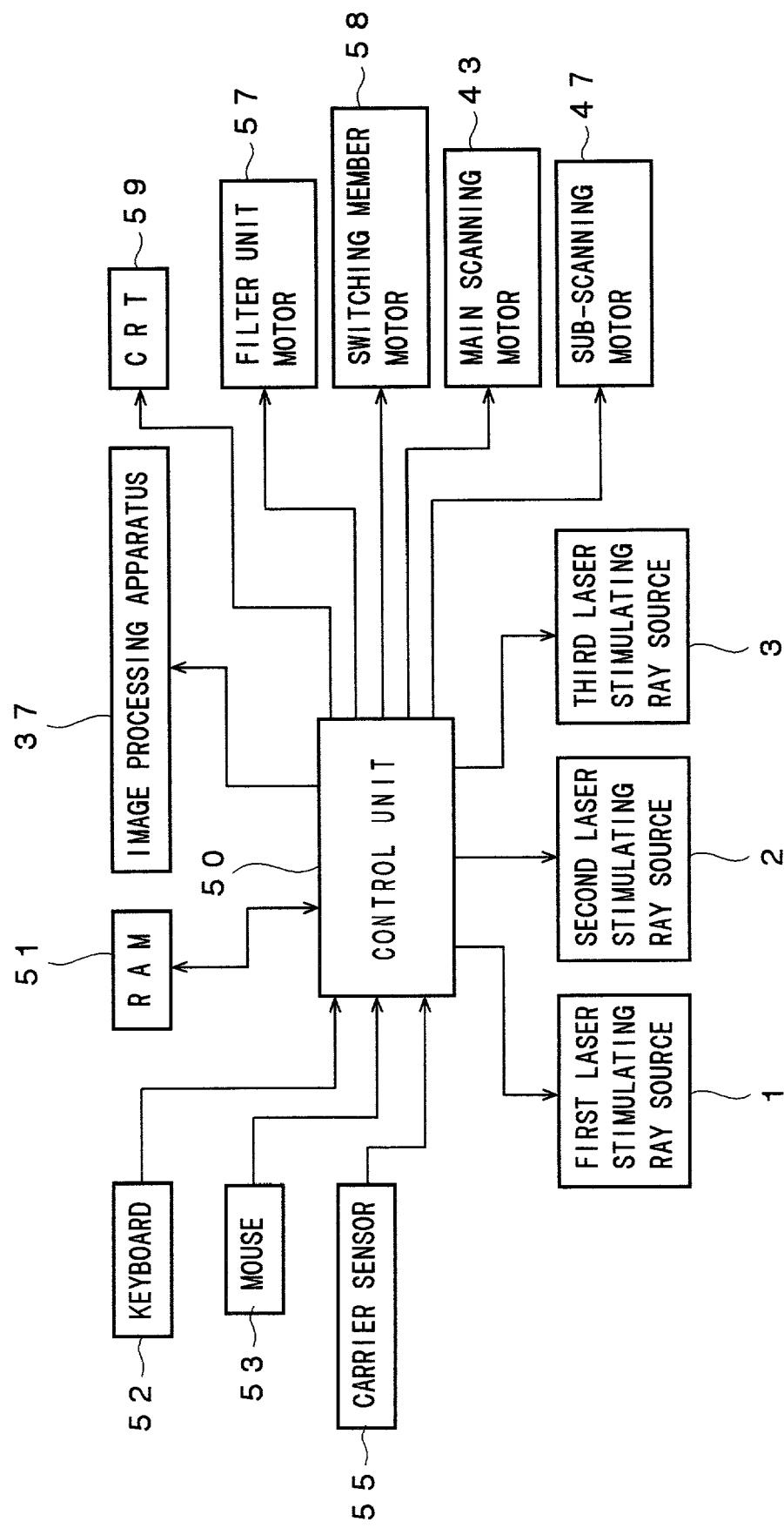
FIG. 4 is a block diagram of a control system, an input system, a detection system, a drive system and a display system of a scanner which is a preferred embodiment of the present invention.

As shown in FIG. 3, a pair of guide rails 41, 41 are fixed on the movable base plate 40 movable in a sub-scanning direction indicated by an arrow Y in FIG. 4 by a sub-scanning motor (not shown) and the sample stage 20 is fixed to three side members 42, 42 (only two shown in FIG. 3.) slidably mounted on the pair of guide rails 41, 41.

As shown in FIG. 3, a main scanning motor 43 is fixed on the movable base plate 40. A timing belt 45 wound around a pulley 44 is wound around the output shaft 43a of the main scanning motor 43 and a rotary encoder 46 is secured to the output shaft 43a of the main scanning motor 43.

Therefore, the sample stage 20 can be reciprocated along the pair of guide rails 41, 41 in the main scanning direction indicated by an arrow X in FIG. 3 by driving the main scanning motor 43 and the sample stage 20 can be two-dimensionally moved by further moving the movable base plate 40 in the sub-scanning direction by the sub-scanning motor (not shown), thereby enabling the whole surface of the sample 22 set on the sample stage 20 to be scanned with the laser beam 4.

The position of the sample stage 20 can be monitored by the rotary encoder 46.

FIG. 4 is a block diagram of a control system, an input system, a detection system, a drive system and a display system of the scanner which is a preferred embodiment of the present invention.

As shown in FIG. 4, the control system of the scanner includes a control unit 50 for controlling the overall operation of the scanner and a RAM 51, and the input system of the scanner includes a keyboard 52 operated by the operator and through which various instruction signal can be input and a mouse 53.

As shown in FIG. 4, the detection system of the scanner includes a carrier sensor 55 for detecting the kind of a sample carrier 21 set on the sample stage 20 and outputting a carrier detection signal to the control unit 50.

As shown in FIG. 4, the drive system of the scanner includes a filter unit motor 57 for moving the filter unit 27 provided with four filters 28a, 28b, 28c, 28d, a switching member motor 58 for moving the confocal switching member 31, the main scanning motor 43 for reciprocating sample stage 20 in the main scanning direction and a sub-scanning motor 47 for intermittently moving the sample stage 20 in the sub-scanning direction.

Further, as shown in FIG. 4, the display system of the scanner includes a CRT 59.

The control unit 50 is constituted so as to selectively output a drive signal to the first laser stimulating ray source 1, the second laser stimulating ray source 2 or the third laser stimulating ray source 3 and also output drive signals to the filter unit motor 57, the switching member motor 58, the main scanning motor 43 and the sub-scanning motor 47.

Figure 5:
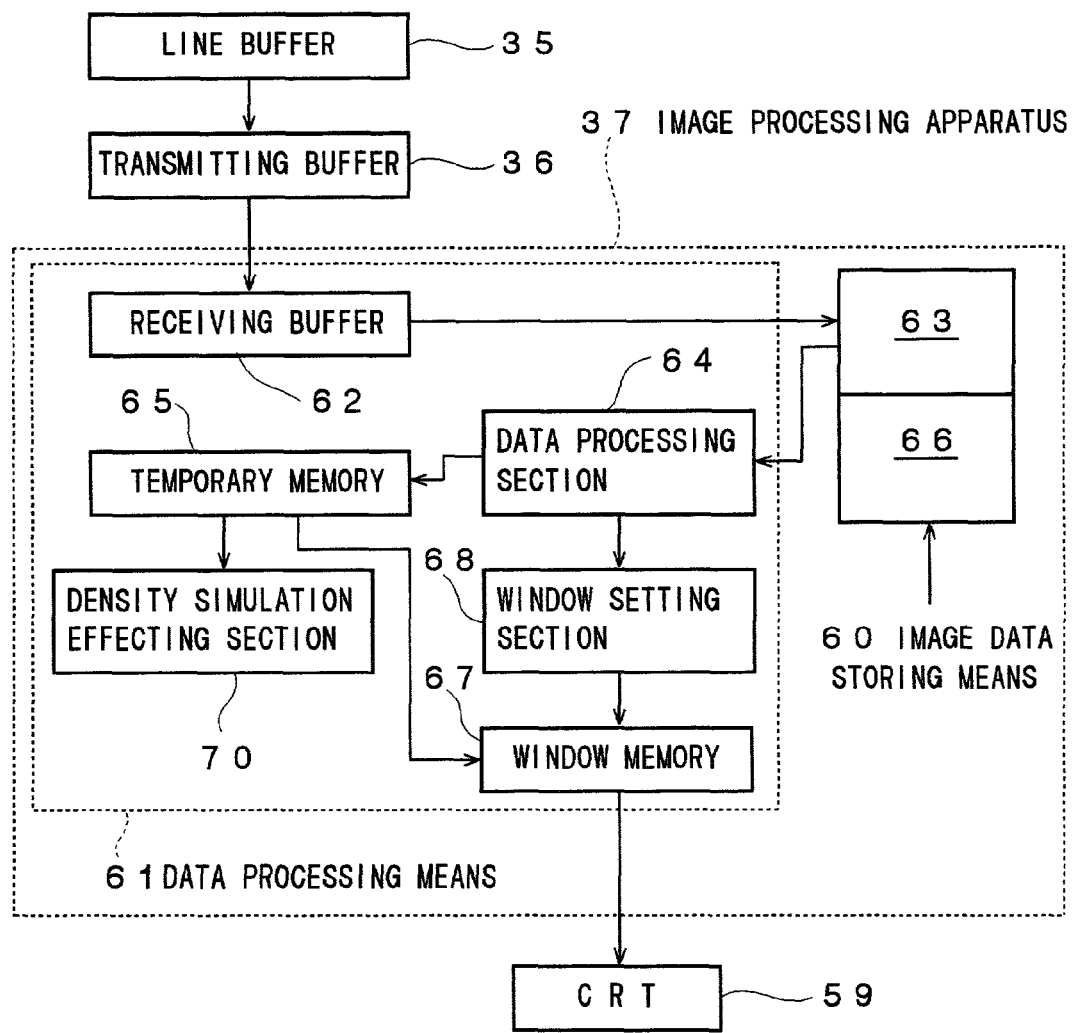
FIG. 5 is a block diagram of an image data processing apparatus of a scanner which is a preferred embodiment of the present invention.

FIG. 5 is a block diagram of the image data processing apparatus 37.

As shown in FIG. 5, the image data processing apparatus 37 of the scanner according to this embodiment includes an image data storing means 60 for storing digital image data and a data processing means 61 for effecting various data processing on digital image data.

The digital image data temporarily stored in the transmitting buffer 36 are input to a receiving buffer 62 in the data processing means 61 of the image data processing apparatus 37 and temporarily stored therein. When a predetermined amount of the image data have been stored in the receiving buffer 62, the stored image data are output to an image data temporary storing section 63 in the image data storing means 60 and stored therein.

In this manner, the image data fed from the transmitting buffer 36 to the receiving buffer 62 of the data processing means 61 and temporarily stored therein are fed from the receiving buffer 62 to the image data temporary storing section 63 in the image data storing means 60 and stored therein.

When the image data obtained by scanning the whole surface of the sample 22 with the laser beam 4 have been stored in the image data temporary storing section 63 in the image data storing means 60, the data processing section 64 in the data processing means 61 reads the image data from the image data temporary storing section 63 and stores them in a temporary memory 65 in the data processing means 61. After the image data have been subjected to necessary data processing in the data processing section 64, the data processing section 64 stores only the processed image data in an image data storing section 66 in the image data storing means 60. The data processing section 64 then erases the image data stored in the image data temporary storing section 63.

As shown in FIG. 5, the data processing means 61 of the image data processing apparatus 37 further includes the receiving buffer 62 for receiving digital image data from the transmitting buffer 36, the data processing section 64 for effecting data processing, the temporary memory 65 for two-dimensionally mapping and temporarily storing digital image data and a window memory 67 for two-dimensionally mapping and temporarily storing digital image data and an image is produced on the screen of the CRT 59 based on the image data two-dimensionally mapped and temporarily stored in the window memory 67.

As shown in FIG. 5, the data processing means 61 of the image data processing apparatus 37 further includes a window setting section 68 for producing various windows, outputting them to the window memory 67 and displaying various windows on the screen of the CRT 59 and a density simulation effecting section 70 described later.

Figure 6:
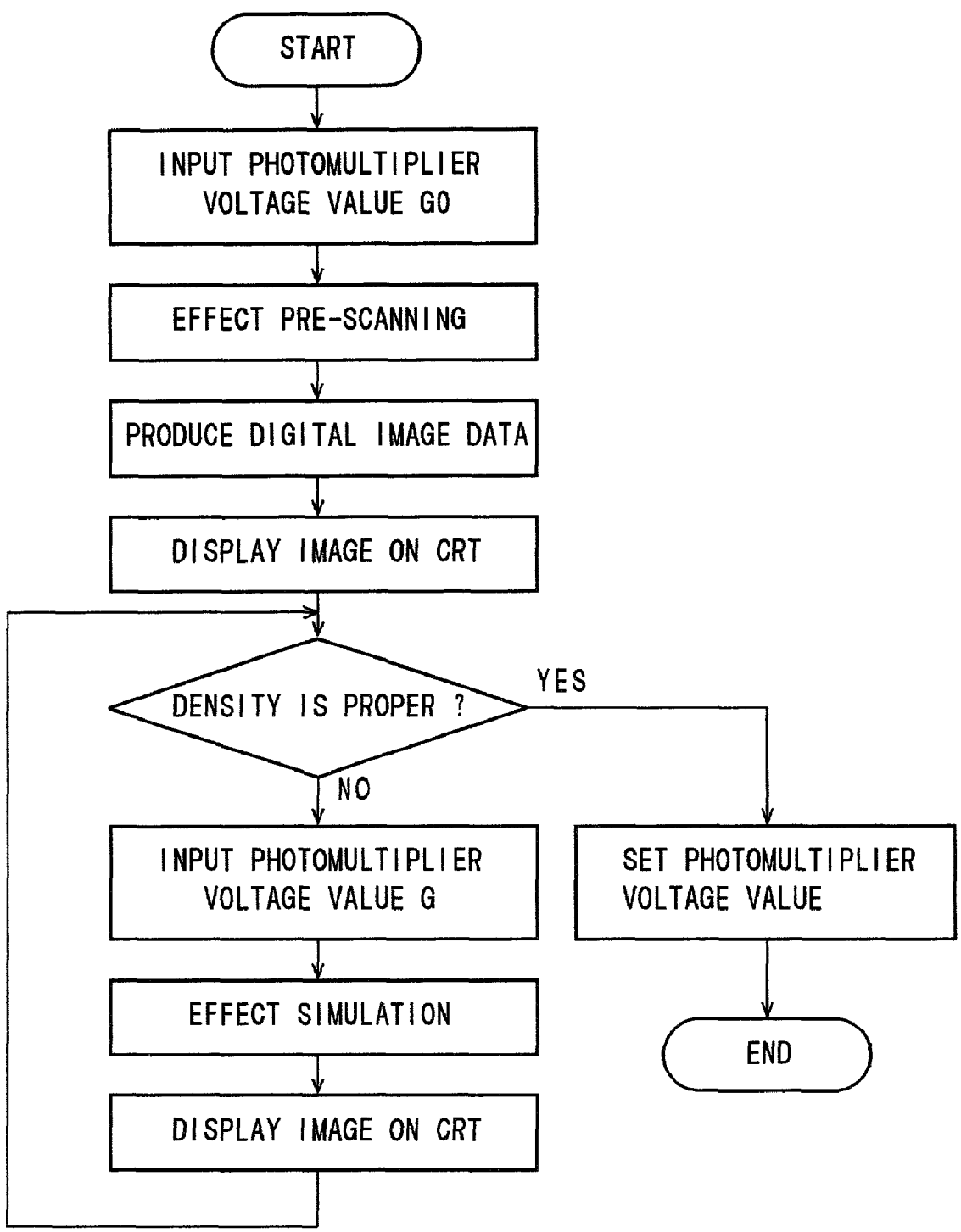
FIG. 6 is a flow chart showing a photomultiplier voltage value G determination routine effected in a scanner which is a preferred embodiment of the present invention.

The thus constituted scanner according to this embodiment effects pre-scanning in accordance with the flow chart shown in FIG. 6 in order to set the voltage value of the photomultiplier 33 prior to scanning the sample 22 with a laser beam 4 to stimulate a labeling substance, photoelectrically detect light released from the labeling substance and produce image data for biochemical analysis.

A sample carrier 21 carrying a micro-array which is a sample 22 is first set by the user on the sample stage 20.

When the sample carrier 21 carrying a micro-array which is a sample 22 is first set on the sample stage 20, the kind of the sample carrier 21 is detected by the carrier sensor 55 and a carrier detection signal is output to the control unit 50.

When the control unit 50 receives the carrier detection signal from the carrier sensor 55, it outputs a drive signal to the switching member motor 58 based on the carrier detection signal and causes it to move the confocal switching member 31 so that the pinhole 32a having the smallest diameter is located in the optical path.

When the kind of a labeling substance, a fluorescent dye and a pre-scanning start signal are input by the user through the keyboard 52, a labeling substance specifying signal and the pre-scanning start signal are input are input from the keyboard 52 to the control unit 50.

In this embodiment, a specimen contained in the micro-array is doubly labeled with Cy3 (registered trademark) and Cy5 (registered trademark) and when one of the fluorescent dyes, for example, Cy5 (registered trademark) is specified by the user through the keyboard 52, since Cy5 is most effectively stimulable with a laser beam 4 having a wavelength of 640 nm, the control unit 50 outputs a drive signal to the filter unit motor 57 in accordance with the input labeling substance specifying signal, thereby causing it to move the filter unit 27 so that the filter 28a having a property to cut off a light component having a wavelength of 640 nm and transmit light components having wavelengths longer than 640 nm is located in the optical path.

When the control unit 50 receives the pre-scanning start signal, it outputs a window setting signal to the window setting section 68 of the data processing means 61 of the image data processing apparatus 37, thereby causing it to produce density simulation window data and output them to the window memory 67 so that a density simulation window is displayed on the screen of the CRT 59.

Figure 7:
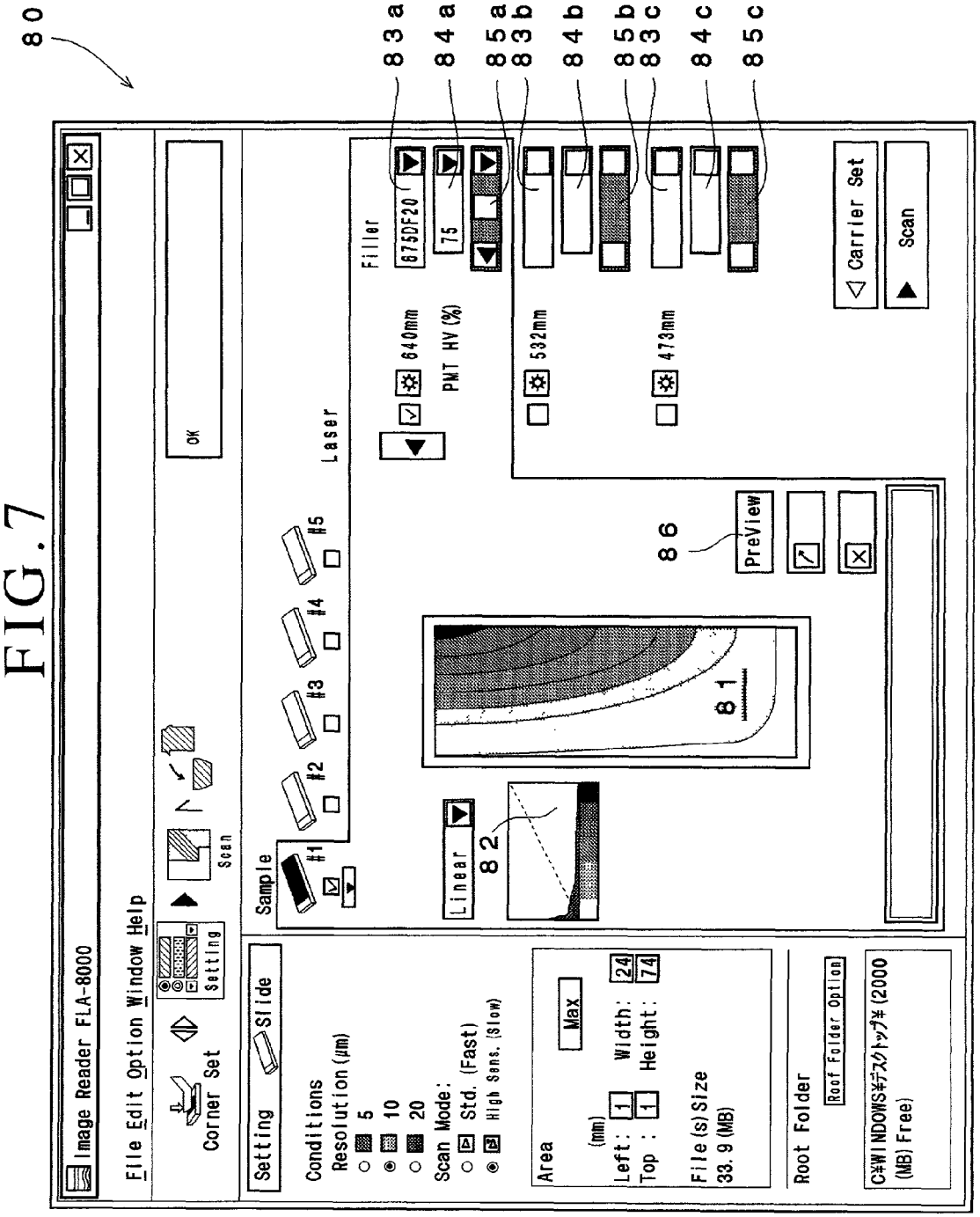
FIG. 7 shows a screen of a CRT on which a density simulation window is displayed.

FIG. 7 shows the screen of the CRT 59 on which the density simulation window is displayed.

As shown in FIG. 7, the density simulation window 80 includes an image display section 81 in which an image produced based on image data is displayed, a gradation display section 82, stimulating ray cut filter display sections 83a, 83b, 83c each displaying the kind of filter used for cutting off a laser beam 4 for one of the laser beam 4 having a wavelength of 640 nm, the laser beam 4 having a wavelength of 532 nm and the laser beam 4 having a wavelength of 473 nm, photomultiplier voltage value display sections 84a, 84b, 84c in which the voltage value of the photomultiplier 33 is displayed, sliders 85a, 85b, 85c for setting the voltage value of the photomultiplier 33 and a pre-scanning button 86, and the voltage value of the photomultiplier 33 input through the keyboard 52 or set by operating the sliders 85a, 85b, 85c is displayed in the photomultiplier voltage value display sections 84a, 84b, 84c.

A moderate but arbitrary photomultiplier voltage value G0 is input through the keyboard 52 or is specified by operating sliders 85a, 85b, 85c using the mouse 53 in the form of a percent value of gain of the photomultiplier 33.

The thus specified photomultiplier voltage value G0 is forwarded to the control unit 50 and the control unit 50 sets the voltage value of the photomultiplier 33 in accordance with the specified photomultiplier voltage value G0 and stores the specified photomultiplier voltage value G0 in the RAM 51.

At the same time, the control unit 50 outputs a data display signal to the window setting section 68 of the image data processing apparatus 37, thereby causing it to display the specified photomultiplier voltage value G0 in the photomultiplier voltage value display section 84a for a laser beam 4 having a wavelength of 640 nm in the density simulation window 80.

The control unit 50 then outputs a drive signal to the first laser stimulating ray source 1 to activate the first laser stimulating ray source 1.

The laser beam 4 emitted from the first laser stimulating ray source 1 passes through a collimator lens 5, thereby being made a parallel beam, and advances to the mirror 6 to be reflected thereby. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the sample 22, the micro-array 22 set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the micro-array set on the sample stage 20 is scanned with the laser beam 4.

When being irradiated with the laser beam 4, Cy5 labeling the probe DNA is stimulated by the laser beam 4, thereby releasing fluorescence emission 25. In the case where a slide glass plate is used as a substrate of the micro-array, since a fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the filter unit 27 has been moved so that the filter 28a is located in the optical path, the fluorescence emission enters the filter 28a, thereby cutting light having a wavelength of 640 nm and transmitting only light having a wavelength longer than 640 nm.

The fluorescence emission transmitted through the filter 28a is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission 25 is focused onto the pinhole 32a and is photoelectrically detected by the photomultiplier 33 thereby producing analog image data.

Fluorescence emission 25 released from a fluorescent dye on the surface of the slide glass plate is led to the photomultiplier 33 using a confocal optical system to be photoelectrically detected in this manner and, therefore, noise in the image data can be minimized.

The analog image data produced by the photomultiplier 33 are converted to digital image data by the A/D converter 34 and the digital image data are forwarded to the line buffer 35 and stored therein.

When the digital image data corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data produced by the pre-scanning and temporarily stored in the transmitting buffer 36 are input to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced by scanning the whole surface of the micro-array with the laser beam 4 emitted from the first laser stimulating ray source 1 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The image data stored in the image data storing section 66 of the image data storing means 60 are read into the temporary memory 65 and two-dimensionally mapped and stored therein. The image data are then read into the window memory 67 and two-dimensionally mapped and stored temporarily therein.

Thus, an image of the specimen labeled with Cy5 is displayed in the image display section 81 in the density simulation window 80 displayed on the screen of the CRT 59 based on the digital image data produced by the pre-scanning and two-dimensionally mapped and temporarily stored in the window memory 67.

However, since the image of the specimen labeled with Cy5 displayed in the image display section 81 in the density simulation window 80 displayed on the screen of the CRT 59 is based on the image data produced using a moderate but arbitrary photomultiplier voltage value G0 specified by the user as the percent value of gain of the photomultiplier 33 and it is extremely difficult for the user to specify a proper photomultiplier voltage value G0 at the stage of the pre-scanning, the image displayed in the image display section 81 in the density simulation window 80 does not have proper density.

Therefore, conventionally, a new photomultiplier voltage value would be specified by the user based on the image displayed on the screen of the CRT 59, thereby again performing the pre-scanning and this operation would be repeated by trial and error until an image having proper density on the screen of the CRT 59. However, such an operation is not only extremely troublesome and time-consuming but also causes degradation of a labeling substance, a fluorescent dye and the amount of fluorescence emission released therefrom as the result of repetition of the pre-scanning.

Therefore, in this embodiment, the data processing means 61 of the image data processing apparatus 37 is provided with a density simulation effecting section 70 so as to enable the user to specify a photomultiplier voltage value G different from that specified prior to the pre-scanning based on the digital image data produced by the pre-scanning by inputting it through the keyboard 52 or operating the slider 65a in the density simulation window 80 displayed on the screen of the CRT 59 using the mouse 53 and simulate the signal intensity, namely, the density of an image that would be produced based on the thus specified photomultiplier voltage value G0.

Figure 8:
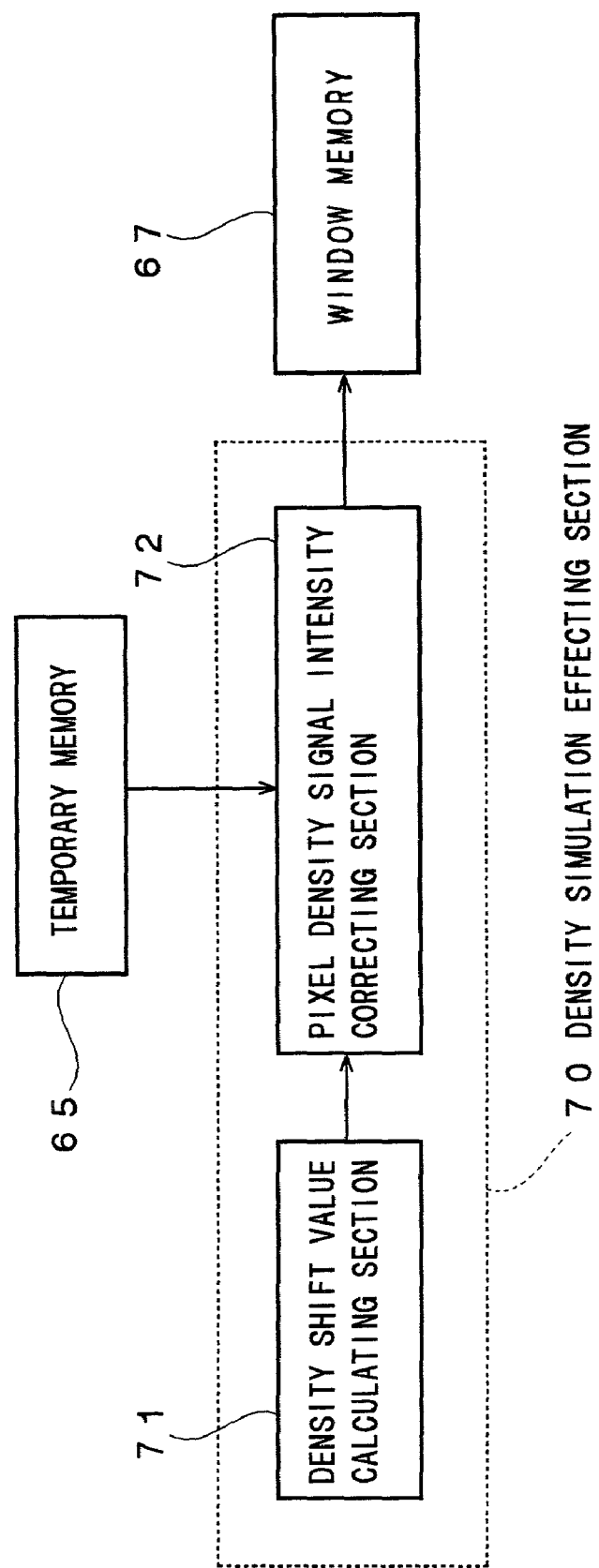
FIG. 8 is a block diagram of a density simulation effecting section provided in a data processing means of an image data processing apparatus of a scanner which is a preferred embodiment of the present invention.

FIG. 8 is a block diagram of the density simulation effecting section 70 provided in the data processing means 61 of the image data processing apparatus 37.

As shown in FIG. 8, the density simulation effecting section 70 provided in the data processing means 61 of the image data processing apparatus 37 includes a density shift value calculating section 71 for calculating a density shift value $\Delta QL$ indicating how a density signal intensity $QLi$ of each pixel in image data produced based on the photomultiplier voltage value G specified by inputting it through the keyboard 52 or operating the slider 65a in the density simulation window 80 displayed on the screen of the CRT 59 using the mouse 53 by the user is shifted from a density signal intensity $QLi0$ of each pixel in the image data produced by the pre-scanning, and a pixel density signal intensity correcting section 72 for correcting the density signal intensity of each pixel constituting the image data produced by the pre-scanning and two-dimensionally mapped and stored in the temporary memory 65 in accordance with the density shift value $\Delta QL$ calculated by the density shift value calculating section 71.

When the user views an image displayed in the image display section 81 in the density simulation window 80 and judges that the density of the image is improper, the user first inputs a photomultiplier voltage value G expected to be proper through the keyboard 52 or inputs a photomultiplier voltage value G expected to be proper by operating the slider 65a in the density simulation window 80 displayed on the screen of the CRT 59 using the mouse 53 and also inputs a density simulation start signal.

The density simulation start signal is input to the control unit 50 together with the photomultiplier voltage value G and in response to the density simulation start signal, the control unit 50 reads the voltage value G0 of the photomultiplier 33 input by the user prior to the pre-scanning and stored in the RAM 51 and outputs it to the image data processing apparatus 37 together with the density simulation start signal and the photomultiplier voltage value G.

At the same time, the control unit 50 stores the newly specified photomultiplier voltage value G in the RAM 51.

The voltage value G0 of the photomultiplier 33, the density simulation start signal and the photomultiplier voltage value G are input to the density shift value calculating section 71 of the density simulation effecting section 70 provided in the data processing means 61 of the image data processing apparatus 37.

When the density shift value calculating section 71 of the density simulation effecting section 70 receives the density simulation start signal, it calculates, based on the photomultiplier voltage value G0 and the photomultiplier voltage value G input from the control unit 50 in accordance with the following formula (1), a density shift value $\Delta QL$ indicating how a density signal intensity $QLi_{640}$ of each pixel in image data produced using the photomultiplier voltage value G specified by the user is shifted from a density signal intensity $QLi0_{640}$ of each pixel in the image data produced by the pre-scanning using the laser beam of a wavelength of 640 nm $$\Delta QL = 2^B/L * \{\log_{10}(G/G0)\} \tag{1}$$

wherein B designates the number of bits and L designates latitude.

Since B=16 and L=5 in this embodiment, the formula (1) can be rewritten as follows $$\Delta QL = 13107.2\{\log_{10}(G/G0)\}.$$

The thus-calculated density shift value $\Delta QL$ is output to the pixel density signal intensity correcting section 72.

On the other hand, the density simulation start signal is also input to the pixel density signal intensity correcting section 72 and when the pixel density signal intensity correcting section 72 receives the density simulation start signal from the control unit 50 and the density shift value $\Delta QL$ from the density shift value calculating section 71, it reads the image data two-dimensionally mapped and temporarily stored in the temporary memory 65. The pixel density signal intensity correcting section 72 then adds the density shift value $\Delta QL$ input from the density shift value calculating section 71 to the density signal intensity $QL0_{640}$ of each pixel in image data produced by the pre-scanning in accordance with the following formula (2), thereby calculating density signal intensity $QLi_{640}$ of each pixel in image data produced using the photomultiplier voltage value G specified by the user $$QLi_{640} = QL0_{640} + \Delta QL \tag{2}$$

The pixel density signal intensity correcting section 72 further assigns the thus-calculated density signal intensity $QLi_{640}$ of each pixel to each of the image data to produce image data in which the density signal intensity of each pixel has been corrected and outputs them to the window memory 67.

The image data in which the density signal intensity of each pixel has been corrected are two-dimensionally mapped and stored in the window memory 67 and an image of the specimen labeled with Cy5 is displayed in the image display section 81 in the density simulation window 80 displayed on the screen of the CRT 59 based on the image data two-dimensionally mapped and stored in the window memory 67.

When the user views the image displayed in the image display section 81 in the density simulation window 80 and judges that the contrast of the image is proper, the user inputs a photomultiplier voltage setting signal through the keyboard 52.

When the control unit 50 receives the photomultiplier voltage setting signal through the keyboard 52, it sets the voltage value of the photomultiplier 33 to be used for producing image data of the specimen labeled with Cy5 based on the photomultiplier voltage value G stored in the RAM 51.

To the contrary, when the user views the image displayed in the image display section 81 in the density simulation window 80 and judges that the contrast of the image is still improper, the user specifies a new voltage value of the photomultiplier 33 though the keyboard 52 or by operating the slider 84a of the density simulation window 80 using the mouse 53 and inputs a density simulation start signal through the keyboard 52.

The density simulation start signal and the newly specified voltage value of the photomultiplier 33 are input to the control unit 50. Similarly to the above, the density shift value $\Delta QL$ is then calculated by the density shift value calculating section 71 and the $QLi_{640}$ of each pixel in image data produced using the photomultiplier voltage value G newly specified by the user and image data in which the density signal intensity of each pixel is corrected are calculated by the pixel density signal intensity correcting section 72. An image of the specimen labeled with Cy5 is then displayed in the image display section 81 in the density simulation window 80 displayed on the screen of the CRT 59 based on the thus produced image data.

In this manner, the density simulation is repeated until an image having proper contrast is displayed in the image display section 81 in the density simulation window 80 displayed on the screen of the CRT 59 so that a photomultiplier voltage value G capable of producing an image of the specimen labeled with Cy5 having proper contrast is determined and that the voltage value of the photomultiplier 33 is set by the control unit 50 based on the thus determined photomultiplier voltage value G.

When the voltage value of the photomultiplier 33 is set by the pre-scanning as described above, the control unit 50 outputs a window close signal to the window setting section 68, thereby causing it to close the density simulation window 80 displayed in the window memory 67. The control unit 50 further outputs a drive signal to the first laser stimulating ray source 1, thereby turning it on and the production of image data of the specimen labeled with Cy5 for biochemical analysis is started.

The laser beam 4 emitted from the first laser stimulating ray source 1 passes through a collimator lens 5, thereby being made a parallel beam, and advances to the mirror 6 to be reflected thereby. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the sample 22, the micro-array set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the micro-array set on the sample stage 20 is scanned with the laser beam 4.

When being irradiated with the laser beam 4, Cy5 labeling the probe DNA is stimulated by the laser beam 4, thereby releasing fluorescence emission 25. In the case where a slide glass plate is used as a substrate of the micro-array, since a fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the filter unit 27 has been moved so that the filter 28a is located in the optical path, the fluorescence emission enters the filter 28a, thereby cutting light having a wavelength of 640 nm and transmitting only light having a wavelength longer than 640 nm.

The fluorescence emission transmitted through the filter 28a is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission 25 is focused onto the pinhole 32a and is photoelectrically detected by the photomultiplier 33 thereby producing analog image data.

Fluorescence emission 25 released from a fluorescent dye on the surface of the slide glass plate is led to the photomultiplier 33 using a confocal optical system to be photoelectrically detected in this manner and, therefore, noise in the image data can be minimized.

The analog image data produced by the photomultiplier 33 are converted to digital image data by the A/D converter 34 and the digital image data are forwarded to the line buffer 35 and stored therein.

When the digital image data corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data produced by the pre-scanning and temporarily stored in the transmitting buffer 36 are input to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced by scanning the whole surface of the micro-array with the laser beam 4 emitted from the first laser stimulating ray source 1 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The image data stored in the image data storing section 66 of the image data storing means 60 are read by the data processing means 61 into the temporary memory 65 and two-dimensionally mapped and stored therein. The image data are data-processed by the data processing means 61 as occasion demands and two-dimensionally mapped and stored temporarily in the window memory 67.

When an image producing signal is input by the user through the keyboard 52, an image of the specimen labeled with Cy5 is displayed on the screen of the CRT 59 based on the image data two-dimensionally mapped and stored temporarily in the window memory 67.

In this embodiment, since the specimen contained in the micro-array is labeled with Cy3® in addition to Cy5®, when the image data of the specimen labeled with Cy5 have been produced, image data of the specimen labeled with Cy3 are produced.

As shown by the formula (1), the density shift value $\Delta QL$ depends upon only the photomultiplier voltage value G and does not depend upon the wavelength of the laser beam 4 used for stimulating a fluorescent dye. However, when the sample 22 set on the sample stage 20 is scanned with a laser beam 4 having a different wavelength, even if the voltage value of the photomultiplier 33 is the same, since the density signal intensity $QLi$ of each pixel in produced digital image data changes, the density signal intensity $QLi0$ of each pixel in image data produced by the pre-scanning changes by setting the voltage value of the photomultiplier 33 to be G0. Therefore, when image data of the specimen labeled with Cy3 for biochemical analysis are to be produced, the pre-scanning is first performed.

When the kind of a labeling substance, a fluorescent dye and a pre-scanning start signal are input by the user through the keyboard 52, a labeling substance specifying signal and the pre-scanning start signal are input from the keyboard 52 to the control unit 50.

When Cy3 is input as the kind of a fluorescent dye, since Cy3 is most effectively stimulable with a laser beam having a wavelength of 473 nm, the control unit 50 outputs a drive signal to the filter unit motor 57 in accordance with the input labeling substance specifying signal, thereby causing it to move the filter unit 27 so that the filter 28c having a property to cut off a light component having a wavelength of 473 nm and transmit light components having wavelengths longer than 473 nm is located in the optical path.

When the control unit 50 receives the pre-scanning start signal, it outputs a window setting signal to the window setting section 68 of the data processing means 61 of the image data processing apparatus 37, thereby causing it to produce density simulation window data and output them to the window memory 67 so that a density simulation window is displayed on the screen of the CRT 59.

A moderate but arbitrary photomultiplier voltage value G0 is then input through the keyboard 52 or is specified by operating the sliders 85c using the mouse 53 by the user in the form of a percent value of gain of the photomultiplier 33.

The thus specified photomultiplier voltage value G0 is forwarded to the control unit 50 and the control unit 50 sets the voltage value of the photomultiplier 33 in accordance with the specified photomultiplier voltage value G0 and stores the specified photomultiplier voltage value G0 in the RAM 51.

At the same time, the control unit 50 outputs a data display signal to the window setting section 68 of the image data processing apparatus 37, thereby causing it to display the specified photomultiplier voltage value G0 in the photomultiplier voltage value display section 84c for a laser beam 4 having a wavelength of 473 nm in the density simulation window 80.

The control unit 50 then outputs a drive signal to the third laser stimulating ray source 3 to activate the third laser stimulating ray source 3.

The laser beam 4 emitted from the third laser stimulating ray source 3 is reflected by the second dichroic mirror 8 to enter the optical head 15.

The laser beam 4 entering the optical unit 15 is reflected by the mirror 16, passes through the hole 17 formed in the perforated mirror 18 and through the lens 19 to impinge on the sample 22, the micro-array set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the micro-array set on the sample stage 20 is scanned with the laser beam 4.

When being irradiated with the laser beam 4, Cy3 labeling the probe DNA is stimulated by the laser beam 4, thereby releasing fluorescence emission 25. In the case where a slide glass plate is used as a substrate of the micro-array, since a fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the filter unit 27 has been moved so that the filter 28c is located in the optical path, the fluorescence emission enters the filter 28c, thereby cutting light having a wavelength of 473 nm and transmitting only light having a wavelength longer than 473 nm.

The fluorescence emission transmitted through the filter 28a is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission 25 is focused onto the pinhole 32a and is photoelectrically detected by the photomultiplier 33 thereby producing analog image data.

Fluorescence emission 25 released from a fluorescent dye on the surface of the slide glass plate is led to the photomultiplier 33 using a confocal optical system to be photoelectrically detected in this manner and, therefore, noise in the image data can be minimized.

The analog image data produced by the photomultiplier 33 are converted to digital image data by the A/D converter 34 and the digital image data are forwarded to the line buffer 35 and stored therein.

When the digital image data corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data produced by the pre-scanning and temporarily stored in the transmitting buffer 36 are input to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced by scanning the whole surface of the micro-array with the laser beam 4 having a wavelength of 473 nm and emitted from the third laser stimulating ray source 3 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The image data stored in the image data storing section 66 of the image data storing means 60 are read into the temporary memory 65 and two-dimensionally mapped and stored therein. The image data are then read into the window memory 67 and two-dimensionally mapped and stored temporarily therein.

Thus, an image of the specimen labeled with Cy5 is displayed in the image display section 81 in the density simulation window 80 displayed on the screen of the CRT 59 based on the digital image data produced by the pre-scanning and two-dimensionally mapped and temporarily stored in the window memory 67.

However, since the image of the specimen labeled with Cy5 displayed in the image display section 81 in the density simulation window 80 displayed on the screen of the CRT 59 is based on the image data produced by using a moderate but arbitrary photomultiplier voltage value G0 specified by the user as the percent value of gain of the photomultiplier 33 and it is extremely difficult for the user to specify a proper photomultiplier voltage value G0 at the stage of the pre-scanning, the image displayed in the image display section 81 in the density simulation window 80 does not have proper density.

Therefore, similarly to the case where the pre-scanning is effected using the laser beam 4 having a wavelength of 640 nm and emitted from the first laser stimulating ray source 1, when the user views an image displayed in the image display section 81 in the density simulation window 80 and judges that the density of the image is improper, the user first inputs a photomultiplier voltage value G expected to be proper through the keyboard 52 or inputs a photomultiplier voltage value G expected to be proper by operating the slider 65a in the density simulation window 80 displayed on the screen of the CRT 59 using the mouse 53 and also inputs a density simulation start signal.

The density simulation start signal is input to the control unit 50 together with the photomultiplier voltage value G and in response to the density simulation start signal, the control unit 50 reads the photomultiplier voltage value G0 input by the user prior to the pre-scanning and stored in the RAM 51 and outputs it to the image data processing apparatus 37 together with the density simulation start signal and the photomultiplier voltage value G.

At the same time, the control unit 50 stores the newly specified photomultiplier voltage value G in the RAM 51.

The photomultiplier voltage value G0, the density simulation start signal and the photomultiplier voltage value G are input to the density shift value calculating section 71 of the density simulation effecting section 70 provided in the data processing means 61 of the image data processing apparatus 37.

When the density shift value calculating section 71 of the density simulation effecting section 70 receives the density simulation start signal, it calculates, based on the photomultiplier voltage value G0 and the photomultiplier voltage value G input from the control unit 50 in accordance with the following formula (1), a density shift value $\Delta QL$ indicating how a density signal intensity $QLi_{473}$ of each pixel in image data produced using the photomultiplier voltage value G specified by the user is shifted from a density signal intensity $QL0_{473}$ of each pixel in the image data produced by the pre-scanning using the laser beam of a wavelength of 473 nm $$\Delta QL = 2^B/L * \{\log_{10}(G/G0)\} \quad (1),$$

wherein B designates the number of bits and L designates latitude.

Since B=16 and L=5 in this embodiment, the formula (1) can be rewritten as follows.

$$\Delta QL = 13107.2\{\log_{10}(G/G0)\}$$

The thus-calculated density shift value $\Delta QL$ is output to the pixel density signal intensity correcting section 72.

On the other hand, the density simulation start signal is also input to the pixel density signal intensity correcting section 72 and when the pixel density signal intensity correcting section 72 receives the density simulation start signal from the control unit 50 and the density shift value $\Delta QL$ from the density shift value calculating section 71, it reads the image data two-dimensionally mapped and temporarily stored in the temporary memory 65. The pixel density signal intensity correcting section 72 then adds the density shift value $\Delta QL$ input from the density shift value calculating section 71 to the density signal intensity $QL0_{473}$ of each pixel in image data produced by the pre-scanning in accordance with the following formula (2), thereby calculating density signal intensity $QLi_{473}$ of each pixel in image data produced using the photomultiplier voltage value G specified by the user $$QLi_{473} = QL0_{473} + \Delta QL \quad (2).$$

The pixel density signal intensity correcting section 72 further assigns the thus-calculated density signal intensity $QLi_{473}$ of each pixel to each of the image data to produce image data in which the density signal intensity of each pixel has been corrected and outputs them to the window memory 67.

The image data in which the density signal intensity of each pixel has been corrected are two-dimensionally mapped and stored in the window memory 67 and an image of the specimen labeled with Cy3 is displayed in the image display section 81 in the density simulation window 80 displayed on the screen of the CRT 59 based on the image data two-dimensionally mapped and stored in the window memory 67.

When the user views the image displayed in the image display section 81 in the density simulation window 80 and judges that the contrast of the image is proper, the user inputs a photomultiplier voltage setting signal through the keyboard 52.

When the control unit 50 receives the photomultiplier voltage setting signal through the keyboard 52, it determines the voltage value of the photomultiplier 33 to be used for producing image data of the specimen labeled with Cy3 based on the photomultiplier voltage value G stored in the RAM 51.

To the contrary, when the user views the image displayed in the image display section 81 in the density simulation window 80 and judges that the contrast of the image is still improper, the user specifies a new voltage value of the photomultiplier 33 though the keyboard 52 or by operating the slider 84a of the density simulation window 80 using the mouse 53 and inputs a density simulation start signal through the keyboard 52.

The density simulation start signal and the newly specified photomultiplier voltage value G are input to the control unit 50. Similarly to the above, the density shift value $\Delta QL$ is then calculated by the density shift value calculating section 71 and the $QLi_{473}$ of each pixel in image data produced using the photomultiplier voltage value G newly specified by the user and image data in which the density signal intensity of each pixel is corrected are calculated by the pixel density signal intensity correcting section 72. An image of the specimen labeled with Cy3 is then displayed in the image display section 81 in the density simulation window 80 displayed on the screen of the CRT 59 based on the thus produced image data.

In this manner, the density simulation is repeated until an image having proper contrast is displayed in the image display section 81 in the density simulation window 80 displayed on the screen of the CRT 59 so that a photomultiplier voltage value G capable of producing an image of the specimen labeled with Cy3 having proper contrast is determined and that the voltage value of the photomultiplier 33 is set by the control unit 50 based on the thus determined photomultiplier voltage value G.

When the voltage value of the photomultiplier 33 is set by the pre-scanning as described above, the control unit 50 outputs a window close signal to the window setting section 68, thereby causing it to close the density simulation window 80 displayed in the window memory 67. The control unit 50 further outputs a drive signal to the third laser stimulating ray source 3, thereby turning it on and the production of image data of the specimen labeled with Cy3 for biochemical analysis is started.

The laser beam 4 emitted from the third laser stimulating ray source 3 is reflected by the second dichroic mirror 8 to enter the optical head 15.

The laser beam 4 entering the optical unit 15 is reflected by the mirror 16, passes through the hole 17 formed in the perforated mirror 18 and through the lens 19 to impinge on the sample 22, the micro-array set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the micro-array set in the sample carrier 21 is scanned with the laser beam 4.

When being irradiated with the laser beam 4, Cy3 labeling the probe DNA is stimulated by the laser beam 4, thereby releasing fluorescence emission 25. In the case where a slide glass plate is used as a substrate of the micro-array, since a fluorescent dye is distributed on only the surface of the slide glass plate, fluorescence emission 25 is released from only the surface of the slide glass plate.

The fluorescence emission 25 released from the slide glass plate passes through the lens 19, thereby being made a parallel beam, and is reflected by the perforated mirror 18, thereby entering the filter unit 27.

Since the filter unit 27 has been moved so that the filter 28c is located in the optical path, the fluorescence emission enters the filter 28c, thereby cutting light having a wavelength of 473 nm and transmitting only light having a wavelength longer than 473 nm.

The fluorescence emission transmitted through the filter 28a is reflected by the mirror 29 and focused by the lens 30.

Since the confocal switching member 31 has been moved prior to the irradiation with the laser beam 4 so that the pinhole 32a having the smallest diameter is located in the optical path, the fluorescence emission 25 is focused onto the pinhole 32a and is photoelectrically detected by the photomultiplier 33 thereby producing analog image data.

Fluorescence emission 25 released from a fluorescent dye on the surface of the slide glass plate is led to the photomultiplier 33 using a confocal optical system to be photoelectrically detected in this manner and, therefore, noise in the image data can be minimized.

The analog image data produced by the photomultiplier 33 are converted to digital image data by the A/D converter 34 and the digital image data are forwarded to the line buffer 35 and stored therein.

When the digital image data corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data produced by the pre-scanning and temporarily stored in the transmitting buffer 36 are input to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced by scanning the whole surface of the micro-array with the laser beam 4 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The image data stored in the image data storing section 66 of the image data storing means 60 are read into the temporary memory 65 and two-dimensionally mapped and stored therein. The image data are then read into the window memory 67 and two-dimensionally mapped and stored temporarily therein.

Thus, an image of the specimen labeled with Cy3 is displayed in the image display section 81 in the density simulation window 80 displayed on the screen of the CRT 59 based on the digital image data produced by the pre-scanning and two-dimensionally mapped and temporarily stored in the window memory 67.

On the other hand, in the case where image data for biochemical analysis are to be produced by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye by a photomultiplier, the image data for biochemical analysis will be produced in the following manner.

As described above, the density shift value $\Delta QL$ depends upon only the photomultiplier voltage value G and does not depend upon the wavelength of a laser beam 4 used for stimulating a fluorescent dye. However, when the sample 22 set on the sample stage 20 is scanned with a laser beam 4 having a different wavelength, even if the voltage value of the photomultiplier 33 is the same, since the density signal intensity $QLi$ of each pixel in produced digital image data changes, the density signal intensity $QLi0$ of each pixel in image data produced by the pre-scanning changes effected by setting the voltage value of the photomultiplier 33 to be G0. Therefore, in the case where image data for biochemical analysis are to be produced by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye by a photomultiplier, when a laser beam 4 having a different wavelength is used, the pre-scanning is first performed.

A sample carrier 21 carrying a fluorescence sample 22 including a transfer support containing denatured DNA fragments selectively labeled with a fluorescent dye as a substrate is first set by the user on the sample stage 20.

When the sample carrier 21 is set on the sample stage 20, the kind of the sample carrier 21 is detected by the carrier sensor 55 and a carrier detection signal is output to the control unit 50.

When the control unit 50 receives the carrier detection signal from the carrier sensor 55, it outputs a drive signal to the switching member motor 58 based on the carrier detection signal and causes it to move the confocal switching member 31 so that the pinhole 32c having the largest diameter is located in the optical path.

When the kind of a labeling substance, a fluorescent dye and a pre-scanning start signal are input by the user through the keyboard 52, a labeling substance specifying signal and the pre-scanning start signal are input are input from the keyboard 52 to the control unit 50.

When the denatured DNA fragments are selectively labeled with Rhodamine®, for example, since Rhodamine can be most effectively stimulated by a laser beam having a wavelength of 532 nm, the control unit 50 selects the second laser stimulating ray source 2 and also outputs a drive signal to the filter unit motor 57, thereby causing it to move the filter unit 27 so that the filter 28a having a property to cut off a light component having a wavelength of 532 nm and transmit light components having wavelengths longer than 532 nm is located in the optical path.

When the control unit 50 receives the pre-scanning start signal, it outputs a window setting signal to the window setting section 68 of the data processing means 61 of the image data processing apparatus 37, thereby causing it to produce a density simulation window data and output them to the window memory 67 so that a density simulation window is displayed on the screen of the CRT 59.

A moderate but arbitrary photomultiplier voltage value G0 is then input through the keyboard 52 or is specified by operating the slider 85*b* using the mouse 53 in the form of a percent value of gain of the photomultiplier 33.

The thus specified photomultiplier voltage value G0 is forwarded to the control unit 50 and the control unit 50 sets the voltage value of the photomultiplier 33 in accordance with the specified photomultiplier voltage value G0 and stores the specified photomultiplier voltage value G0 in the RAM 51.

At the same time, the control unit 50 outputs a data display signal to the window setting section 68 of the image data processing apparatus 37, thereby causing it to display the specified photomultiplier voltage value G0 in the photomultiplier voltage value display section 84*b* for a laser beam 4 having a wavelength of 532 nm in the density simulation window 80.

The control unit 50 then outputs a drive signal to the second laser stimulating ray source 2 to activate the second laser stimulating ray source 2.

The laser beam 4 emitted from the second laser stimulating ray source 2 passes through a collimator lens 9, thereby being made a parallel beam, and advances to the first dichroic mirror 7 to be reflected thereby.

The laser beam 4 reflected by the first dichroic mirror 7 passes through the second dichroic mirror 8 and enters the optical head 15.

The laser beam 4 entering the optical unit 15 is reflected by the mirror 16, passes through the hole 17 formed in the perforated mirror 18 and through the lens 19 to impinge on the fluorescence sample 22 set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the fluorescence sample 22 set in the sample carrier 21 is scanned with the laser beam 4.

When being irradiated with the laser beam 4, the fluorescent dye labeling the specimen, for example, Rhodamine, is stimulated by the laser beam 4, thereby releasing fluorescence emission 25. In the case where a transfer support is used as a substrate of the fluorescence sample 22, since a fluorescent dye is distributed in the depth direction of the transfer support, fluorescence emission 25 is released from a predetermined region in the depth direction of the transfer support and the positions of the light emitting points fluctuate in the depth direction.

The fluorescence emission 25 released from the fluorescence sample 22 using the transfer support as a substrate passes through the lens 19, thereby being made a parallel beam, and is reflected by the perforated mirror 18, thereby entering the filter unit 27.

Since the filter unit 27 has been moved so that the filter 28*b* is located in the optical path, the fluorescence emission enters the filter 28*b*, thereby cutting light having a wavelength of 532 nm and transmitting only light having a wavelength longer than 532 nm.

The fluorescence emission transmitted through the filter 28*b* is reflected by the mirror 29 and condensed by the lens 30. However, since the fluorescence emission is released from a predetermined region in the depth direction of the transfer support, the fluorescence emission is not focused.

Since the confocal switching member 31 has been moved prior to the irradiation with the laser beam 4 so that the pinhole 32*c* having the largest diameter is located in the optical path, the fluorescence emission 25 passes through the pinhole 32*b* and is photoelectrically detected by the photomultiplier 33 thereby producing analog image data.

Therefore, although the confocal optical system is employed for detecting fluorescence emission 25 released from a fluorescent dye on the surface of the micro-array using the slide glass plate as a substrate with a high S/N ratio, fluorescence emission 25 released from a predetermined region in the depth direction of the transfer support can be detected with high signal intensity.

The analog image data produced by the photomultiplier 33 are converted to digital image data by the A/D converter 34 and the digital image data are forwarded to the line buffer 35 and stored therein.

When the digital image data produced by the pre-scanning and corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data produced by the pre-scanning and temporarily stored in the transmitting buffer 36 are input to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced at the pre-scanning by scanning the whole surface of the micro-array with the laser beam 4 having a wavelength of 532 nm and emitted from the second laser stimulating ray source 2 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The image data stored in the image data storing section 66 of the image data storing means 60 are read into the temporary memory 65 and two-dimensionally mapped and stored therein. The image data are then read into the window memory 67 and two-dimensionally mapped and stored temporarily therein.

Thus, an image of the denatured DNA fragments selectively labeled with Rhodamine is displayed in the image display section 81 in the density simulation window 80 displayed on the screen of the CRT 59 based on the digital image data produced by the pre-scanning and two-dimensionally mapped and temporarily stored in the window memory 67.

As described above, however, since the image of the denatured DNA fragments selectively labeled with Rhodamine displayed in the image display section 81 in the density simulation window 80 displayed on the screen of the CRT 59 is based on the image data produced by using a moderate but arbitrary photomultiplier voltage value G0 specified by the user as the percent value of gain of the photomultiplier 33 and it is extremely difficult for the user to specify a proper photomultiplier voltage value G0 at the stage of the pre-scanning, the image displayed in the image display section 81 in the density simulation window 80 does not have proper density.

Therefore, similarly to the case where the pre-scanning is effected using the laser beam 4 having a wavelength of 640 nm and emitted from the first laser stimulating ray source 1, when the user views an image displayed in the image display section 81 in the density simulation window 80 and judges that the density of the image is improper, the user first inputs a photomultiplier voltage value G expected to be proper through the keyboard 52 or inputs a photomultiplier voltage value G expected to be proper by operating the slider 65a in the density simulation window 80 displayed on the screen of the CRT 59 using the mouse 53 and also inputs a density simulation start signal.

The density simulation start signal is input to the control unit 50 together with the photomultiplier voltage value G and in response to the density simulation start signal, the control unit 50 reads the photomultiplier voltage value G0 input by the user prior to the pre-scanning and stored in the RAM 51 and outputs it to the image data processing apparatus 37 together with the density simulation start signal and the photomultiplier voltage value G.

At the same time, the control unit 50 stores the newly specified photomultiplier voltage value G in the RAM 51.

The photomultiplier voltage value G0, the density simulation start signal and the photomultiplier voltage value G are input to the density shift value calculating section 71 of the density simulation effecting section 70 provided in the data processing means 61 of the image data processing apparatus 37.

When the density shift value calculating section 71 of the density simulation effecting section 70 receives the density simulation start signal, it calculates, based on the photomultiplier voltage value G0 and the photomultiplier voltage value G input from the control unit 50 in accordance with the following formula (1), a density shift value $\Delta QL$ indicating how a density signal intensity $QLi_{532}$ of each pixel in image data produced using the photomultiplier voltage value G specified by the user is shifted from a density signal intensity $QLi0_{532}$ of each pixel in the image data produced by the pre-scanning using the laser beam of a wavelength of 532 nm $$\Delta QL = 2^B/L * \{\log_{10}(G/G0)\} \quad (1),$$

wherein B designates the number of bits and L designates latitude.

Since B=16 and L=5 in this embodiment, the formula (1) can be rewritten as follows $$\Delta QL = 13107.2\{\log_{10}(G/G0)\}.$$

The thus-calculated density shift value $\Delta QL$ is output to the pixel density signal intensity correcting section 72.

On the other hand, the density simulation start signal is also input to the pixel density signal intensity correcting section 72 and when the pixel density signal intensity correcting section 72 receives the density simulation start signal from the control unit 50 and the density shift value $\Delta QL$ from the density shift value calculating section 71, it reads the image data two-dimensionally mapped and temporarily stored in the temporary memory 65. The pixel density signal intensity correcting section 72 then adds the density shift value $\Delta QL$ input from the density shift value calculating section 71 to the density signal intensity $QL0_{532}$ of each pixel in image data produced by the pre-scanning in accordance with the following formula (2), thereby calculating density signal intensity $QLi_{532}$ of each pixel in image data produced using the photomultiplier voltage value G specified by the user $$QLi_{532} = QL0_{532} + \Delta QL \quad (2).$$

The pixel density signal intensity correcting section 72 further assigns the thus-calculated density signal intensity $QLi_{532}$ of each pixel to each of the image data to produce image data in which the density signal intensity of each pixel has been corrected and outputs them to the window memory 67.

The image data in which the density signal intensity of each pixel has been corrected are two-dimensionally mapped and stored in the window memory 67 and an image of the denatured DNA fragments selectively labeled with Rhodamine is displayed in the image display section 81 in the density simulation window 80 displayed on the screen of the CRT 59 based on the image data two-dimensionally mapped and stored in the window memory 67.

When the user views the image displayed in the image display section 81 in the density simulation window 80 and judges that the contrast of the image is proper, the user inputs a photomultiplier voltage setting signal through the keyboard 52.

When the control unit 50 receives the photomultiplier voltage setting signal through the keyboard 52, it determines the voltage value of the photomultiplier 33 to be used for producing image data of the denatured DNA fragments selectively labeled with Rhodamine based on the photomultiplier voltage value G stored in the RAM 51.

To the contrary, when the user views the image displayed in the image display section 81 in the density simulation window 80 and judges that the contrast of the image is still improper, the user specifies a new voltage value of the photomultiplier 33 though the keyboard 52 or by operating the slider 84b of the density simulation window 80 using the mouse 53 and inputs a density simulation start signal through the keyboard 52.

The density simulation start signal and the newly specified photomultiplier voltage value G are input to the control unit 50. Similarly to the above, the density shift value $\Delta QL$ is then calculated by the density shift value calculating section 71 and the $QLi_{532}$ of each pixel in image data produced using the photomultiplier voltage value G newly specified by the user and image data in which the density signal intensity of each pixel is corrected are calculated by the pixel density signal intensity correcting section 72. An image of the denatured DNA fragments selectively labeled with Rhodamine is then displayed in the image display section 81 in the density simulation window 80 displayed on the screen of the CRT 59 based on the thus produced image data.

In this manner, the density simulation is repeated until an image having proper contrast is displayed in the image display section 81 in the density simulation window 80 displayed on the screen of the CRT 59 so that a photomultiplier voltage value G capable of producing an image of the specimen labeled with Cy3 having proper contrast is determined and that the voltage value of the photomultiplier 33 is set by the control unit 50 based on the thus determined photomultiplier voltage value G.

When the voltage value of the photomultiplier 33 is set by the pre-scanning as described above, the control unit 50 outputs a window close signal to the window setting section 68, thereby causing it to close the density simulation window 80 displayed in the window memory 67. The control unit 50 further outputs a drive signal to the second laser stimulating ray source 2, thereby turning it on and the production of image data of the denatured DNA fragments selectively labeled with Rhodamine for biochemical analysis is started.

The laser beam 4 emitted from the second laser stimulating ray source 2 passes through a collimator lens 9, thereby being made a parallel beam, and advances to the first dichroic mirror 7 to be reflected thereby.

The laser beam 4 reflected by the first dichroic mirror 7 passes through the second dichroic mirror 8 and enters the optical head 15.

The laser beam 4 entering the optical unit 15 is reflected by the mirror 16, passes through the hole 17 formed in the perforated mirror 18 and through the lens 19 to impinge on the fluorescence sample 22 set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the fluorescence sample 22 set in the sample carrier 21 is scanned with the laser beam 4.

When being irradiated with the laser beam 4, the fluorescent dye labeling the specimen, for example, Rhodamine is stimulated by the laser beam 4, thereby releasing fluorescence emission 25. In the case where a transfer support is used as a substrate of the fluorescence sample 22, since a fluorescent dye is distributed in the depth direction of the transfer support, fluorescence emission 25 is released from a predetermined region in the depth direction of the transfer support and the positions of the light emitting points fluctuate in the depth direction.

The fluorescence emission 25 released from the fluorescence sample 22 using the transfer support as a substrate passes through the lens 19, thereby being made a parallel beam, and is reflected by the perforated mirror 18, thereby entering the filter unit 27.

Since the filter unit 27 has been moved so that the filter 28b is located in the optical path, the fluorescence emission enters the filter 28b, thereby cutting light having a wavelength of 532 nm and transmitting only light having a wavelength longer than 532 nm.

The fluorescence emission transmitted through the filter 28b is reflected by the mirror 29 and condensed by the lens 30 however, since the fluorescence emission is released from a predetermined region in the depth direction of the transfer support, the fluorescence emission is not focused.

Since the confocal switching member 31 has been moved prior to the irradiation with the laser beam 4 so that the pinhole 32c having the largest diameter is located in the optical path, the fluorescence emission 25 passes through the pinhole 32b and is photoelectrically detected by the photomultiplier 33 thereby producing analog image data.

Therefore, although the confocal optical system is employed for detecting fluorescence emission 25 released from a fluorescent dye on the surface of the micro-array using the slide glass plate as a substrate with a high S/N ratio, fluorescence emission 25 released from a predetermined region in the depth direction of the transfer support can be detected with high signal intensity.

The analog image data produced by the photomultiplier 33 are converted to digital image data by the A/D converter 34 and the digital image data are forwarded to the line buffer 35 and stored therein.

When the thus produced digital image data corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data are input from the transmitting buffer 36 to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced by scanning the whole surface of the micro-array with the laser beam 4 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The digital image data are read from the image data storing section 66 into the temporary memory 65 to be two-dimensionally mapped and stored therein and are read into the window memory 67 to be two-dimensionally mapped and temporarily stored therein. An image of the denatured DNA fragments selectively labeled with Rhodamine is displayed on the screen of the CRT 59 based on the image data two-dimensionally mapped and temporarily stored in the window memory 67.

To the contrary, in the case where image data for biochemical analysis are to be produced by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor, biochemical analysis data regarding locational information of a radioactive labeling substance will be produced.

As described above, the density shift value $\Delta$ QL depends upon only the photomultiplier voltage value G and does not depend upon the wavelength of a laser beam 4 used for stimulating a fluorescent dye. However, when the sample 22 set on the sample stage 20 is scanned with a laser beam 4 having a different wavelength, even if the voltage value of the photomultiplier 33 is the same, since the density signal intensity $QL_i$ of each pixel in produced digital image data changes, the density signal intensity $QL_{i0}$ of each pixel in image data produced by the pre-scanning changes by setting the voltage value of the photomultiplier 33 to be G0. Therefore, in the case where image data for biochemical analysis are to be produced by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor, when a laser beam 4 having a different wavelength is used, the pre-scanning is first performed.

However, in this embodiment, the pre-scanning has been completed using the laser beam 4 emitted from the first laser stimulating ray source 1 and the photomultiplier voltage value G capable of producing image data based on which an image having proper density can be produced has been determined by the density simulation prior to the production of the image data of the specimen contained in the micro-array and labeled with Cy5 for biochemical analysis, although a stimulable phosphor can be most efficiently stimulated by a laser beam 4 having a wavelength of 640 nm and emitted from the first laser stimulating ray source 1. Therefore, in the case where image data for biochemical analysis are to be produced by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor, since the voltage value of the photomultiplier 33 has been set in accordance with the photomultiplier voltage value G determined by the density simulation effected prior to the production of the image data of the specimen contained in the micro-array and labeled with Cy5 for biochemical analysis, the pre-scanning is not performed prior to the production of image data regarding locational information of a radioactive labeling substance for biochemical analysis.

A sample carrier 21 carrying a stimulable phosphor sheet formed with a stimulable phosphor layer is first set by the user on the sample stage 20.

When the sample carrier 21 is set on the sample stage 20, the kind of the sample carrier 21 is detected by the carrier sensor 55 and a carrier detection signal is output to the control unit 50.

When the control unit 50 receives the carrier detection signal from the carrier sensor 55, it outputs a drive signal to the switching member motor 58 based on the carrier detection signal and causes it to move the confocal switching member 31 so that the pinhole 32b having an intermediate diameter is located in the optical path.

The control unit 50 further outputs a drive signal to the filter unit motor 57 in accordance with the carrier detection signal, thereby causing it to move the filter unit 27 so that the filter 28d having a property to transmit only a light component having a wavelength of the stimulated emission and to cut off a light component having a wavelength of 640 nm is located in the optical path.

The control unit 50 then outputs a drive signal to the first laser stimulating ray source 1, thereby turning it on.

A laser beam 4 emitted from the first laser stimulating ray source 1 passes through a collimator lens 5, thereby being made a parallel beam, and is reflected by the mirror 6. The laser beam 4 reflected by the mirror 6 passes through the first dichroic mirror 7 and the second dichroic mirror 8 and enters the optical head 15.

The laser beam 4 entering the optical unit 15 is reflected by the mirror 16, passes through the hole 17 formed in the perforated mirror 18 and through the lens 19 to impinge on the sample 22, i.e., the stimulable phosphor sheet, set on the sample stage 20.

Since the sample stage 20 is moved by the main scanning motor 43 in the main scanning direction indicated by an arrow X in FIG. 3 and is moved by the sub-scanning motor 47 in the sub-scanning direction indicated by an arrow Y in FIG. 3, the whole surface of the stimulable phosphor layer of the stimulable phosphor sheet set in the sample carrier 21 is scanned with the laser beam 4.

When being irradiated with the laser beam 4, a stimulable phosphor contained in the stimulable phosphor layer is excited by the laser beam 4, thereby releasing stimulated emission 25. In the stimulable phosphor sheet, since a stimulable phosphor is contained in the stimulable phosphor layer and is distributed in the depth direction of the stimulable phosphor layer to some extent, stimulated emission is released from a predetermined region in the depth direction of the stimulable phosphor layer and the positions of the light emitting points fluctuate in the depth direction. However, since the stimulable phosphor layer is thin, the distribution of the light emitting points in the depth direction is not so great as that for reading a fluorescent image carried in the transfer support.

The stimulated emission 25 released from the stimulable phosphor layer passes through the lens 19, thereby being made a parallel beam, and is reflected by the perforated mirror 18, thereby entering the filter unit 27.

Since the filter unit 27 has been moved so that the filter 28d is located in the optical path, the stimulated emission enters the filter 28d, thereby cutting light having a wavelength of 640 nm and transmitting only light having a wavelength of the stimulated emission released from the stimulable phosphor.

The stimulated emission 25 transmitted through the filter 28d is reflected by the mirror 29 and condensed by the lens 30. However, since the stimulated emission is released from a predetermined region in the depth direction of the stimulable phosphor layer, it is not focused.

Since the confocal switching member 31 has been moved prior to the irradiation with the laser beam 4 so that the pinhole 32b having an intermediate diameter is located in the optical path, the stimulated emission 25 passes through the pinhole 32b and is photoelectrically detected by the photomultiplier 33 thereby producing analog image data.

Therefore, although the confocal optical system is employed for detecting fluorescence emission 25 released from a fluorescent dye on the surface of the micro-array using the slide glass plate as a substrate with a high S/N ratio, stimulated emission 25 released from a predetermined region in the depth direction of the stimulable phosphor layer formed on the stimulable phosphor sheet can be detected with high signal intensity.

The analog image data produced by the photomultiplier 33 are converted to digital image data by the A/D converter 34 and the digital image data are forwarded to the line buffer 35 and stored therein.

When the digital image data corresponding to one scanning line have been stored in the line buffer 35, the line buffer 35 outputs the digital image data to the transmitting buffer 36 whose capacity is greater than that of the line buffer 35 and when the transmitting buffer 36 has stored a predetermined amount of the digital image data, it outputs the digital image data to an image data processing apparatus 37.

The digital image data are input from the transmitting buffer 36 to a receiving buffer 62 in the data processing means 61 of the image data processing apparatus 37 and temporarily stored therein. When a predetermined amount of the image data have been stored in the receiving buffer 62, the stored image data are output to the image data temporary storing section 63 of the image data storing means 60 and stored therein.

In this manner, when the digital image data produced by scanning the whole surface of the stimulable phosphor layer of the stimulable phosphor sheet with the laser beam 4 have been stored in the image data temporary storing section 63 of the image data storing means 60, the data processing section 64 of the data processing means 61 reads the digital image data from the image data temporary storing section 63 and stores them in the temporary memory 65 in the data processing means 61. After the data processing section 64 has effected necessary data processing on the digital image data, it stores only the processed digital image data in the image data storing section 66 in the image data storing means 60. The data processing section 64 then erases the digital image data stored in the image data temporary storing section 63.

The digital image data stored in the image data storing section 66 of the image data storing means 60 are read into the temporary memory 65 to be two-dimensionally mapped and stored therein and are read into the window memory 68 to be two-dimensionally mapped and temporarily stored therein. An image regarding locational information of a radioactive labeling substance is then displayed on the screen of the CRT 59 based on the digital image data two-dimensionally mapped and temporarily stored in the window memory 68.

According to the above described embodiment, a proper photomultiplier voltage value G is determined for each wavelength of laser beams 4 used for stimulating a labeling substance contained in the sample 22 by calculating, based on image data produced by a pre-scanning operation using a moderate but arbitrary photomultiplier voltage value G0, the contrast of image data obtained by scanning the sample 22 with a laser beam 4 to stimulate a labeling substance and photoelectrically detecting light released from the labeling substance by a photomultiplier 33 whose photomultiplier voltage value is set to be different from the photomultiplier voltage value G0, and simulating the density of an image. Therefore, since it is unnecessary to repeat the pre-scanning operation for determining a proper photomultiplier voltage value G, it is possible to not only rapidly determine the voltage value of the photomultiplier 33 in a desired manner with a simple operation but also prevent a fluorescent dye labeling a specimen from being repeatedly irradiated with the laser beam 4 and degraded and an amount of fluorescence emission to be detected from being lowered when image data for biochemical analysis are produced. It is possible to further prevent the stimulable phosphor layer from being repeatedly irradiated with the laser beam 4, the radiation energy stored in the stimulable phosphor layer from being lost and an amount of stimulated emission to be detected from being lowered when image data for biochemical analysis are produced.

Furthermore, according to the above described embodiment, since an image expected to be produced using a photomultiplier voltage value specified by the user is displayed in the image display section 81 in the density simulation window 80 on the screen of the CRT 59, the user can visibly judge whether or not the specified photomultiplier voltage value G is proper and a proper photomultiplier voltage value can be very simply determined.

Moreover, according to the above described embodiment, since an image expected to be produced using a photomultiplier voltage value specified by the user is displayed on the screen of the CRT 59, when inter-picture operation has to be performed between image data that would be produced by scanning a micro-array labeled with two or more kinds of fluorescent dyes which are effectively stimulated by laser beams 4 having different wavelengths from each other, it is possible to effectively perform inter-picture operation between images produced using laser beams 4 having different wavelengths from each other by setting the photomultiplier voltage value G so that the density of specific spots is the same between images labeled with fluorescent dyes without coinciding the density of the specific spots by image data processing after image data were produced.

The present invention has thus been shown and described with reference to specific embodiments. However, it should be noted that the present invention is in no way limited to the details of the described arrangements but changes and modifications may be made without departing from the scope of the appended claims.

For example, in the above described embodiment, although the density shift value calculating section 71 is constituted so as to calculate the shift value Δ QL of the density signal intensity of each pixel in accordance with the following formula (1) wherein the input photomultiplier voltage value is G0, the photomultiplier voltage value G based on which the contrast of an image that would be produced is simulated, the number of bits is B and the latitude is L, it is not absolutely necessary to calculate the shift value Δ QL of the density signal intensity of each pixel in accordance with the following formula (1) and it is possible to simulate the contrast of an image that would be produced when the photomultiplier voltage value is set G by experimentally obtaining the formula representing the relationship between the photomultiplier voltage value is G0, the photomultiplier voltage value G and the shift value Δ QL of the density signal intensity of each pixel for each scanner to be used and calculating the shift value A QL of the density signal intensity of each pixel $$\Delta QL = 2^B/L * \{\log_{10}(G/G0)\} (1).$$

Further, in the above described embodiment, the scanner is constituted so as to produce image data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye, further to produce image data for biochemical analysis by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye, and to produce image data for biochemical analysis by scanning a stimulable phosphor layer of a stimulable phosphor sheet in which locational information of a radioactive labeling substance is recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor. However, it is sufficient for the scanner to be able to produce image data for biochemical analysis by scanning a micro-array including a slide glass plate on which a number of spots of a specimen selectively labeled with a fluorescent dye are formed as a substrate with a laser beam 4 to stimulate the fluorescent dye and photoelectrically detecting fluorescence emission released from the fluorescent dye and it is not absolutely necessary for the scanner to be further constituted so as to produce image data for biochemical analysis by scanning a fluorescence sample including a transfer support containing denatured DNA fragments selectively labeled with a fluorescent dye as a substrate with a laser beam 4 to stimulate the fluorescent dye and photoelectrically detecting fluorescence emission released from the fluorescent dye, and to produce image data for biochemical analysis by scanning a stimulable phosphor layer of a stimulable phosphor sheet in which locational information of a radioactive labeling substance are recorded by closely contacting a substrate such as a membrane filter having a number of spots of a specimen selectively labeled with a radioactive labeling substance and the stimulable phosphor sheet formed with the stimulable phosphor layer containing a stimulable phosphor to expose the stimulable phosphor layer with the radioactive labeling substance with a laser beam 4 to excite the stimulable phosphor and photoelectrically detecting stimulated emission released from the stimulable phosphor.

Furthermore, in the above described embodiment, although the specimen is labeled with two kinds of fluorescent dyes, namely, Cy5 (registered trademark) and Cy3 (registered trademark), it is not absolutely necessary for the specimen to be labeled with two kinds of fluorescent dyes and the specimen may be labeled with one kind of fluorescent dye or three or more kinds of fluorescent dyes.

Moreover, in the above described embodiment, although the scanner includes the first laser stimulating ray source 1, the second laser stimulating ray source 2 and the third laser stimulating ray source 3, it is not absolutely necessary for the scanner to include three laser stimulating ray sources.

Further, in the above described embodiment, although a semiconductor laser beam source for emitting a laser beam 4 having a wavelength of 640 nm is employed as the first laser stimulating ray source 1, a He—Ne laser beam source for emitting a laser beam 4 having a wavelength of 633 nm or a semiconductor laser beam source for emitting a laser beam 4 having a wavelength of 635 nm may be employed instead of the semiconductor laser beam source for emitting a laser beam 4 having a wavelength of 640 nm.

Furthermore, in the above described embodiment, a laser beam source for emitting a laser beam 4 having a wavelength of 532 nm is used as the second laser stimulating ray source 2 and a laser beam source for emitting a laser beam 4 having a wavelength of 473 nm is used as the third laser stimulating ray source 3. However, depending upon the kind of a fluorescent substance, a laser beam source for emitting a laser beam 4 having a wavelength of 530 to 540 nm may be used as the second laser stimulating ray source 2 and a laser beam source for emitting a laser beam 4 having a wavelength of 470 to 480 nm may be used as the third laser stimulating ray source 3.

In addition, in the above described embodiment, the confocal switching member 31 is formed with three pinholes 32a, 32b, 32c having different diameters from each other so that when biochemical analysis data are to be produced by scanning the micro-array 22 in which a plurality of spots of a specimen selectively labeled with a fluorescent dye are formed on the slide glass plate 23 to stimulate the fluorescent dye and photoelectrically detecting fluorescence emission released from the fluorescent dye, the pinhole 32a is used, when biochemical analysis data are to be produced by scanning the stimulable phosphor layer of the stimulable phosphor sheet in which locational information of a radioactive labeling substance obtained by exposing the stimulable phosphor layer to radiation is recorded with a laser beam 4 to stimulate a stimulable phosphor and photoelectrically detecting stimulated emission released from the stimulable phosphor, the pinhole 32b is used and when biochemical analysis data are to be produced by scanning the fluorescence sample including a transfer support with a laser beam 4 to stimulate the fluorescent dye and photoelectrically detecting fluorescence emission released from the fluorescent dye, the pinhole 32c is used. However, it is possible to form only the pinholes 32a, 32b in the confocal switching member 31 so that when biochemical analysis data are to be produced by scanning the micro-array 22 in which a plurality of spots of a specimen selectively labeled with a fluorescent dye are formed on the slide glass plate 23 to stimulate the fluorescent dye and photoelectrically detecting fluorescence emission 25 released from the fluorescent dye, fluorescence emission 25 is detected through the pinhole 32a, when biochemical analysis data are to be produced by photoelectrically detecting stimulated emission 25 released from the stimulable phosphor layer, the stimulated emission 25 is detected through the pinhole 32b and when biochemical analysis data are to be produced by photoelectrically detecting fluorescence emission 25 released from the fluorescence sample including the transfer support as a substrate, the confocal switching member 31 is retracted from the optical path of fluorescence emission 25, thereby increasing a light amount received by the photomultiplier 33, and it is also possible to form only the pinhole 32a in the confocal switching member 31 so that only when biochemical analysis data are to be produced by scanning the micro-array 22 in which a plurality of spots of a specimen selectively labeled with a fluorescent dye are formed on the slide glass plate 23 to stimulate the fluorescent dye and photoelectrically detecting fluorescence emission 25 released from the fluorescent dye, fluorescence emission 25 is detected through the pinhole 32a and when biochemical analysis data are to be produced by photoelectrically detecting stimulated emission 25 released from the stimulable phosphor layer and when biochemical analysis data are to be produced by photoelectrically detecting fluorescence emission 25 released from the fluorescence sample including the transfer support as a substrate, the confocal switching member 31 is retracted from the optical path of fluorescence emission 25, thereby increasing a light amount received by the photomultiplier 33.

Moreover, although an image is displayed on the screen of the CRT 63 in the above described embodiment, a display means for displaying an image is not limited to the CRT 63 and instead of a CRT 63, a flat display panel such as a liquid crystal display panel, an organic EL display panel or the like may be used.

According to the present invention, it is possible to provide a scanner and a method for setting a voltage value of a photomultiplier which can determine the voltage value of the photomultiplier simply and rapidly without causing on the degradation of a sample.

The invention claimed is:

1. A scanner comprising:
at least one laser stimulating ray source for emitting a laser beam,
a sample stage on which a sample containing a labeling substance is to be placed,
a scanning means for moving the sample stage so that the sample placed on the sample stage can be scanned with the laser beam emitted from the at least one laser stimulating ray source,
a photomultiplier for photoelectrically detecting light released from the labeling substance contained in the sample upon being scanned with the laser beam and producing analog image data, and an A/D converter for converting the analog image data produced by the photomultiplier to digital image data;

the scanner further comprising pixel density signal intensity simulating means for effecting simulation based on pre-scan digital image data produced by setting a voltage value of the photomultiplier to a given photomultiplier voltage value G0, scanning the sample placed on the sample stage with the laser beam emitted from the at least one laser stimulating ray source, thereby effecting pre-scanning, and photoelectrically detecting light released from the labeling substance contained in the sample as a result of the pre-scanning by the photomultiplier, which simulation uses the pre-scan digital image data produced when the voltage value of the photomultiplier is set to G0 to simulate density signal intensity of each pixel of digital image data that would be produced by setting the photomultiplier to a voltage value G different from the voltage value G0, scanning the sample placed on the sample stage with the laser beam emitted from the at least one laser stimulating ray source, photoelectrically detecting light released from the labeling substance contained in the sample by the photomultiplier whose voltage value is set to G to produce analog image data, and digitizing the analog image data by the A/D converter, wherein the pixel density signal intensity simulating means comprises density signal intensity shift value calculating means for calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter from the density signal intensity of each pixel of the digital image data produced by the pre-scanning, and pixel density signal intensity correcting means for correcting the density signal intensity of each pixel of the digital image data produced by the pre-scanning based on the density signal intensity shift value calculated by the density signal intensity shift value calculating means and simulating density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter, and wherein the density signal intensity shift value calculating means is constituted so as to calculate a density signal intensity shift value $\Delta QL$ of each pixel in accordance with the following formula:

$$\Delta QL = 2^B/L*\{log_{10}(G/G0)\}$$

wherein G0 is the given photomultiplier voltage value, G is a photomultiplier voltage value different from the given photomultiplier voltage value G0, B is the number of bits and L is latitude.

2. A scanner in accordance with claim 1 wherein the pixel density signal intensity correcting means is constituted so as to simulate, in accordance with the following formula, density signal intensity $QLi_\lambda$, $QLi_\lambda = QLi0_\lambda + \Delta QL$, of each pixel of digital image data that would be produced by photoelectrically detecting light released from the sample by the photomultiplier set to a photomultiplier voltage value G different from the given photomultiplier voltage value G0 to produce analog image data and digitizing the analog image data by the A/D converter, wherein $QLi0_\lambda$ is density signal intensity of each pixel of the digital image data produced by the pre-scanning and $\lambda$ is a wavelength of the laser beam emitted from the at least one laser stimulating ray source.

3. A method for setting a voltage value of a photomultiplier comprising the steps of:

setting a voltage value of a photomultiplier to a given photomultiplier voltage value G0, scanning a sample containing a labeling substance and placed on a sample stage with a laser beam, thereby effecting pre-scanning, photoelectrically detecting light released from the labeling substance contained in the sample as a result of the pre-scanning by the photomultiplier set to the given photomultiplier voltage value G0 to produce analog image data, digitizing the analog image data by an A/D converter to produce digital image data, simulating, based on density signal intensity of each pixel of the digital image data produced by the pre-scanning, density signal intensity of each pixel of digital image data that would be produced by scanning the sample placed on the sample stage with a laser beam, photoelectrically detecting light released from the labeling substance contained in the sample by the photomultiplier set to a photomultiplier voltage value G different from the given photomultiplier voltage value G0 to produce analog image data and digitizing the analog image data by the A/D converter, determining a photomultiplier voltage value G of the photomultiplier in accordance with the simulated density signal intensity of each pixel of the digital image data, and setting the voltage value of the photomultiplier;

wherein the method for setting a voltage value of a photomultiplier further comprises the steps of calculating a density signal intensity shift value of density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter from the density signal intensity of each pixel of the digital image data produced by the pre-scanning, correcting the density signal intensity of each pixel of digital image data produced by the pre-scanning in accordance with the density signal intensity shift value, and simulating density signal intensity of each pixel of digital image data that would be produced by scanning the sample placed on the sample stage with the laser beam emitted from the at least one laser stimulating ray source, photoelectrically detecting light released from the labeling substance contained in the sample by the photomultiplier set to a photomultiplier voltage value G different from the given photomultiplier voltage value G0 to produce analog image data, and digitizing the analog image data by the A/D converter;

wherein a density signal intensity shift value $\Delta QL$ of each pixel is calculated in accordance with the following formula:

$$\Delta QL = 2^B/L * \{log_{10}(G/G0)\}$$

wherein G0 is the given photomultiplier voltage value, G is a photomultiplier voltage value different from the given photomultiplier voltage value G0, B is the number of bits and L is latitude.

4. A method for setting a voltage value of a photomultiplier in accordance with claim 3 wherein density signal intensity $QLi_\lambda$, $QLi_\lambda = QLi0_\lambda + \Delta QL$ of each pixel of digital image data that would be produced by photoelectrically detecting light released from the sample by the photomultiplier set to a photomultiplier voltage value G different from the given photomultiplier voltage value G0 to produce analog image data and digitizing the analog image data by the A/D converter is simulated in accordance with the following formula wherein $QLi0_\lambda$ is density signal intensity of each pixel of the digital image data produced by the pre-scanning and $\lambda$ is a wavelength of the laser beam emitted from the at least one laser stimulating ray source.

* * * * *